(12) United States Patent
Patel et al.

(10) Patent No.: US 12,137,907 B2
(45) Date of Patent: Nov. 12, 2024

(54) SURGICAL STAPLER HANDLE ASSEMBLY HAVING ACTUATION MECHANISM WITH LONGITUDINALLY ROTATABLE SHAFT

(71) Applicant: Applied Medical Resources Corporation, Rancho Santa Margarita, CA (US)

(72) Inventors: Atal C. Patel, Mission Viejo, CA (US); Jonathan Covach, Mission Viejo, CA (US); Christina N. Reed, Trabuco Canyon, CA (US); Gary M. Johnson, Rancho Santa Margarita, CA (US); Matthew M. Becerra, Lake Forest, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 0 days.

(21) Appl. No.: 18/494,610

(22) Filed: Oct. 25, 2023

(65) Prior Publication Data
US 2024/0050092 A1      Feb. 15, 2024

Related U.S. Application Data

(63) Continuation of application No. 17/980,395, filed on Nov. 3, 2022, now Pat. No. 11,844,491, which is a
(Continued)

(51) Int. Cl.
*A61B 17/072*    (2006.01)
*A61B 17/00*     (2006.01)
*A61B 17/068*    (2006.01)

(52) U.S. Cl.
CPC .............. *A61B 17/07207* (2013.01); *A61B 2017/0046* (2013.01); *A61B 2017/00477* (2013.01); *A61B 17/068* (2013.01); *A61B 2017/07257* (2013.01)

(58) Field of Classification Search
CPC ............ A61B 17/07207; A61B 17/068; A61B 2017/0046; A61B 2017/00477; A61B 2017/07257
See application file for complete search history.

(56) References Cited

U.S. PATENT DOCUMENTS 2,073,960 A    3/1937   Crosby
2,140,593 A   12/1938   Pankonin
(Continued)

FOREIGN PATENT DOCUMENTS

EP    0 251 444 A1    1/1988
EP    0 492 283 A1    7/1992
(Continued)

OTHER PUBLICATIONS

Ethicon Endo Surgery, Inc., Contour Curved Cutter Stapler, 2014.
(Continued)

*Primary Examiner* — Veronica Martin
(74) *Attorney, Agent, or Firm* — John F. Heal

(57) ABSTRACT

A handle assembly for a surgical stapler can comprise a rotatable actuation shaft. The actuation shaft can have a first rotational orientation in which it can actuate a jaw assembly in a repeatable open and close mode, a second rotational orientation in which it can actuate a jaw assembly in a staple firing mode, and a third rotational orientation in which it can actuate a jaw assembly in a reversing mode. The handle assembly can include a rotational mechanism arranged to discretely position the rotatable actuation shaft in one of the rotational orientations. The rotational mechanism can be arranged for single handed operation such as by including a slidable switch or selector to rotate the actuation shaft.

20 Claims, 18 Drawing Sheets

Related U.S. Application Data continuation of application No. 17/141,050, filed on Jan. 4, 2021, now Pat. No. 11,529,141, which is a continuation of application No. 16/789,152, filed on Feb. 12, 2020, now Pat. No. 10,912,565, which is a continuation of application No. 15/598,458, filed on May 18, 2017, now Pat. No. 10,595,866, which is a continuation of application No. 14/213,493, filed on Mar. 14, 2014, now Pat. No. 9,668,732.

(60) Provisional application No. 61/794,700, filed on Mar. 15, 2013.

(56) References Cited

U.S. PATENT DOCUMENTS

| | | | |
|---|---|---|---|
| 2,351,608 | A | 6/1944 | Greenwood |
| 2,487,565 | A | 11/1949 | Leber et al. |
| 2,641,154 | A | 6/1953 | Heller |
| 3,076,373 | A | 2/1963 | Matthews |
| 3,077,812 | A | 2/1963 | Dietrich |
| 3,080,564 | A | 3/1963 | Strekopitov et al. |
| 3,203,220 | A | 8/1965 | Kaepernik |
| 3,252,643 | A | 5/1966 | Strekopitov et al. |
| 3,273,562 | A | 9/1966 | Brown |
| 3,373,646 | A | 3/1968 | Ehlert |
| 3,459,187 | A | 8/1969 | Pallotta |
| 3,494,533 | A | 2/1970 | Green et al. |
| 3,662,939 | A | 5/1972 | Bryan |
| 3,675,688 | A | 7/1972 | Bryan et al. |
| 3,692,224 | A | 9/1972 | Astafiev et al. |
| 4,261,244 | A | 4/1981 | Becht et al. |
| 4,281,785 | A | 8/1981 | Brooks |
| 4,304,236 | A | 12/1981 | Conta et al. |
| 4,312,363 | A | 1/1982 | Rothfuss et al. |
| 4,317,451 | A | 3/1982 | Cerwin et al. |
| 4,407,286 | A | 10/1983 | Noiles et al. |
| 4,434,796 | A | 3/1984 | Karapetian et al. |
| 4,442,964 | A | 4/1984 | Becht |
| 4,454,875 | A | 6/1984 | Pratt et al. |
| 4,522,327 | A | 6/1985 | Korthoff et al. |
| 4,527,724 | A | 7/1985 | Chow et al. |
| 4,589,582 | A | 5/1986 | Bilotti |
| 4,591,085 | A | 5/1986 | Di Giovanni |
| 4,606,344 | A | 8/1986 | Di Giovanni |
| 4,608,981 | A | 9/1986 | Rothfuss et al. |
| 4,610,383 | A | 9/1986 | Rothfuss et al. |
| 4,728,020 | A | 3/1988 | Green et al. |
| 4,805,823 | A | 2/1989 | Rothfuss |
| 4,892,244 | A | 1/1990 | Fox et al. |
| 4,923,350 | A | 5/1990 | Hinksman et al. |
| 4,941,623 | A | 7/1990 | Pruitt |
| 4,955,959 | A | 9/1990 | Tompkins et al. |
| 4,978,049 | A | 12/1990 | Green |
| 5,031,814 | A | 7/1991 | Tompkins et al. |
| 5,065,929 | A | 11/1991 | Schulze et al. |
| 5,071,052 | A | 12/1991 | Rodak et al. |
| 5,106,008 | A | 4/1992 | Tompkins et al. |
| 5,116,349 | A | 5/1992 | Aranyi |
| 5,129,570 | A | 7/1992 | Schulze et al. |
| 5,201,746 | A | 4/1993 | Shichman |
| 5,221,036 | A | 6/1993 | Takase |
| 5,236,440 | A | 8/1993 | Hlavacek |
| 5,240,163 | A | 8/1993 | Stein et al. |
| RE34,519 | E | 1/1994 | Fox et al. |
| 5,275,323 | A | 1/1994 | Schulze et al. |
| 5,289,963 | A | 3/1994 | McGarry et al. |
| D347,474 | S | 5/1994 | Olson |
| 5,307,976 | A | 5/1994 | Olson et al. |
| 5,308,576 | A | 5/1994 | Green et al. |
| 5,326,013 | A | 7/1994 | Green et al. |
| 5,350,400 | A | 9/1994 | Esposito et al. |
| 5,360,305 | A | 11/1994 | Kerrigan |
| 5,364,002 | A | 11/1994 | Green et al. |
| 5,366,479 | A | 11/1994 | McGarry et al. |
| 5,381,943 | A | 1/1995 | Allen et al. |
| 5,389,098 | A | 2/1995 | Tsuruta et al. |
| 5,395,034 | A | 3/1995 | Allen et al. |
| 5,397,046 | A | 3/1995 | Savage et al. |
| 5,413,267 | A | 5/1995 | Solyntjes et al. |
| 5,415,334 | A | 5/1995 | Williamson, IV et al. |
| 5,415,335 | A | 5/1995 | Knodell, Jr. |
| 5,439,155 | A | 8/1995 | Viola |
| 5,439,479 | A | 8/1995 | Shichman et al. |
| 5,445,304 | A | 8/1995 | Plyley et al. |
| 5,447,265 | A | 9/1995 | Vidal et al. |
| 5,452,836 | A | 9/1995 | Huitema et al. |
| 5,456,401 | A | 10/1995 | Green et al. |
| 5,458,279 | A | 10/1995 | Plyley |
| 5,462,215 | A | 10/1995 | Viola et al. |
| 5,464,144 | A | 11/1995 | Guy et al. |
| 5,465,895 | A | 11/1995 | Knodel et al. |
| 5,470,006 | A | 11/1995 | Rodak |
| 5,470,007 | A | 11/1995 | Plyley et al. |
| 5,470,008 | A | 11/1995 | Rodak |
| 5,470,009 | A | 11/1995 | Rodak |
| 5,472,132 | A | 12/1995 | Savage et al. |
| 5,480,089 | A | 1/1996 | Blewett |
| 5,485,952 | A | 1/1996 | Fontayne |
| 5,487,500 | A | 1/1996 | Knodel et al. |
| 5,489,058 | A | 2/1996 | Plyley |
| 5,497,933 | A | 3/1996 | DeFonzo et al. |
| 5,507,426 | A | 4/1996 | Young et al. |
| 5,507,773 | A | 4/1996 | Hultema et al. |
| 5,509,596 | A | 4/1996 | Green et al. |
| 5,509,920 | A | 4/1996 | Phillips et al. |
| 5,529,235 | A | 6/1996 | Boiarski et al. |
| 5,547,117 | A | 8/1996 | Hamblin et al. |
| 5,553,765 | A | 9/1996 | Knodel et al. |
| 5,554,164 | A | 9/1996 | Wilson et al. |
| 5,558,266 | A | 9/1996 | Green et al. |
| 5,562,241 | A | 10/1996 | Knodel et al. |
| 5,562,700 | A | 10/1996 | Huitema et al. |
| 5,562,701 | A | 10/1996 | Huitema et al. |
| 5,562,702 | A | 10/1996 | Huitema et al. |
| 5,564,615 | A | 10/1996 | Bishop et al. |
| 5,571,115 | A | 11/1996 | Nicholas |
| 5,571,285 | A | 11/1996 | Chow et al. |
| 5,579,978 | A | 12/1996 | Green et al. |
| 5,580,067 | A | 12/1996 | Hamblin et al. |
| 5,584,425 | A | 12/1996 | Savage et al. |
| 5,586,711 | A | 12/1996 | Plyley et al. |
| 5,588,581 | A | 12/1996 | Conlon et al. |
| 5,597,107 | A | 1/1997 | Knodel et al. |
| 5,601,224 | A | 2/1997 | Bishop et al. |
| 5,605,272 | A | 2/1997 | Witt et al. |
| 5,607,095 | A | 3/1997 | Smith et al. |
| 5,615,820 | A | 4/1997 | Viola |
| 5,626,587 | A | 5/1997 | Bishop et al. |
| 5,630,539 | A | 5/1997 | Plyley et al. |
| 5,634,584 | A | 6/1997 | Okorocha et al. |
| 5,636,779 | A | 6/1997 | Palmer |
| 5,657,921 | A | 8/1997 | Young et al. |
| 5,662,258 | A | 9/1997 | Knodel et al. |
| 5,662,662 | A | 9/1997 | Bishop et al. |
| 5,662,667 | A | 9/1997 | Knodel |
| 5,673,840 | A | 10/1997 | Schulze et al. |
| 5,673,841 | A | 10/1997 | Schulze et al. |
| 5,673,842 | A | 10/1997 | Bittner et al. |
| 5,676,674 | A | 10/1997 | Bolanos et al. |
| 5,678,748 | A | 10/1997 | Plyley |
| 5,680,982 | A | 10/1997 | Schulze et al. |
| 5,680,983 | A | 10/1997 | Plyley et al. |
| 5,697,542 | A | 12/1997 | Knodel et al. |
| 5,697,543 | A | 12/1997 | Burdorff |
| 5,704,534 | A | 1/1998 | Huitema et al. |
| 5,704,898 | A | 1/1998 | Kokish |
| 5,706,998 | A | 1/1998 | Blyley et al. |
| 5,709,334 | A | 1/1998 | Sorrentino et al. |
| 5,713,505 | A | 2/1998 | Hultema |
| 5,715,988 | A | 2/1998 | Palmer |
| 5,718,359 | A | 2/1998 | Palmer et al. |
| 5,732,871 | A | 3/1998 | Clark et al. |
| 5,735,445 | A | 4/1998 | Vidal et al. |

(56) References Cited

U.S. PATENT DOCUMENTS

| | | |
|---|---|---|
| 5,762,255 A | 6/1998 | Chrisman et al. |
| 5,762,256 A | 6/1998 | Mastri et al. |
| 5,779,130 A | 7/1998 | Alesi et al. |
| 5,782,396 A | 7/1998 | Mastri et al. |
| 5,782,397 A | 7/1998 | Koukline |
| 5,785,232 A | 7/1998 | Vidal et al. |
| 5,794,834 A | 8/1998 | Hamblin et al. |
| 5,797,536 A | 8/1998 | Smith et al. |
| 5,797,537 A | 8/1998 | Oberlin et al. |
| 5,797,538 A | 8/1998 | Heaton et al. |
| 5,810,240 A | 9/1998 | Robertson |
| 5,814,055 A | 9/1998 | Knodel et al. |
| 5,820,009 A | 10/1998 | Melling et al. |
| 5,829,662 A | 11/1998 | Allen et al. |
| 5,860,995 A | 1/1999 | Berkelaar |
| 5,865,361 A | 2/1999 | Milliman et al. |
| 5,878,937 A | 3/1999 | Green et al. |
| 5,878,938 A | 3/1999 | Bittner et al. |
| 5,893,506 A | 4/1999 | Powell |
| 5,894,979 A | 4/1999 | Powell |
| 5,901,895 A | 5/1999 | Heaton et al. |
| 5,918,791 A | 7/1999 | Sorrentino et al. |
| 5,931,847 A | 8/1999 | Bittner et al. |
| 5,954,259 A | 9/1999 | Viola et al. |
| 5,964,394 A | 10/1999 | Robertson |
| D416,089 S | 11/1999 | Barton et al. |
| 5,988,479 A | 11/1999 | Palmer |
| 6,032,849 A | 3/2000 | Mastri et al. |
| 6,053,390 A | 4/2000 | Green et al. |
| 6,079,606 A | 6/2000 | Milliman et al. |
| 6,109,500 A | 8/2000 | Alli et al. |
| 6,131,789 A | 10/2000 | Schulze et al. |
| 6,155,473 A | 12/2000 | Tompkins et al. |
| D441,865 S | 5/2001 | Racenet et al. |
| 6,241,139 B1 | 6/2001 | Milliman et al. |
| 6,250,532 B1 | 6/2001 | Green et al. |
| 6,264,087 B1 | 7/2001 | Whitman |
| 6,270,453 B1 | 8/2001 | Sakai |
| 6,325,810 B1 | 12/2001 | Hamilton et al. |
| 6,330,965 B1 | 12/2001 | Milliman et al. |
| 6,488,196 B1 | 12/2002 | Fenton, Jr. |
| 6,550,757 B2 | 4/2003 | Sesek |
| 6,569,171 B2 | 5/2003 | DeGuillebon et al. |
| 6,595,509 B2 | 7/2003 | Sesek |
| 6,619,529 B2 | 9/2003 | Green et al. |
| 6,644,532 B2 | 11/2003 | Green et al. |
| 6,669,073 B2 | 12/2003 | Milliman et al. |
| 6,716,233 B1 | 4/2004 | Whitman |
| 6,786,382 B1 | 9/2004 | Hoffman |
| 6,817,508 B1 | 11/2004 | Racenet et al. |
| 6,821,282 B2 | 11/2004 | Perry et al. |
| 6,835,199 B2 | 12/2004 | McGuckin, Jr. et al. |
| 6,913,181 B2 | 7/2005 | Mochizuki et al. |
| 6,923,360 B2 | 8/2005 | Sesek et al. |
| 6,953,138 B1 | 10/2005 | Dworak et al. |
| 6,953,139 B2 | 10/2005 | Milliman et al. |
| 6,964,363 B2 | 11/2005 | Wales et al. |
| 6,978,921 B2 | 12/2005 | Shelton, IV et al. |
| 6,986,451 B1 | 1/2006 | Mastri et al. |
| 6,988,649 B2 | 1/2006 | Shelton, IV et al. |
| 7,000,818 B2 | 2/2006 | Shelton, IV et al. |
| 7,044,352 B2 | 5/2006 | Shelton, IV et al. |
| 7,044,353 B2 | 5/2006 | Mastri et al. |
| 7,044,947 B2 | 5/2006 | de la Torre et al. |
| 7,055,730 B2 | 6/2006 | Ehrenfels et al. |
| 7,070,083 B2 | 7/2006 | Jankowski |
| 7,097,089 B2 | 8/2006 | Marczyk |
| 7,097,650 B2 | 8/2006 | Weller et al. |
| 7,108,472 B2 | 9/2006 | Norris et al. |
| 7,128,253 B2 | 10/2006 | Mastri et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,147,139 B2 | 12/2006 | Schwemberger et al. |
| 7,213,736 B2 | 5/2007 | Wales et al. |
| 7,225,964 B2 | 6/2007 | Mastri et al. |
| 7,237,708 B1 | 7/2007 | Guy et al. |
| 7,258,262 B2 | 8/2007 | Mastri et al. |
| 7,275,674 B2 | 10/2007 | Racenet et al. |
| 7,278,562 B2 | 10/2007 | Mastri et al. |
| 7,290,692 B2 | 11/2007 | Marks |
| 7,293,685 B2 | 11/2007 | Ehrenfels et al. |
| 7,303,107 B2 | 12/2007 | Milliman et al. |
| 7,308,998 B2 | 12/2007 | Mastri et al. |
| 7,328,828 B2 | 2/2008 | Ortiz et al. |
| 7,334,717 B2 | 2/2008 | Rethy et al. |
| 7,380,695 B2 | 6/2008 | Doll et al. |
| 7,380,696 B2 | 6/2008 | Shelton, IV et al. |
| 7,398,908 B2 | 7/2008 | Holsten et al. |
| 7,399,310 B2 | 7/2008 | Edoga et al. |
| 7,401,721 B2 | 7/2008 | Holsten et al. |
| 7,404,508 B2 | 7/2008 | Smith et al. |
| 7,407,075 B2 | 8/2008 | Holsten et al. |
| 7,407,078 B2 | 8/2008 | Shelton, IV et al. |
| 7,416,101 B2 | 8/2008 | Shelton, IV et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,422,136 B1 | 9/2008 | Marczyk |
| 7,422,139 B2 | 9/2008 | Shelton, IV et al. |
| 7,431,188 B1 | 10/2008 | Marczyk |
| 7,434,715 B2 | 10/2008 | Shelton, IV et al. |
| 7,434,716 B2 | 10/2008 | Viola |
| 7,455,208 B2 | 11/2008 | Wales et al. |
| 7,455,676 B2 | 11/2008 | Holsten et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,481,348 B2 | 1/2009 | Marczyk |
| 7,481,349 B2 | 1/2009 | Holsten et al. |
| 7,487,899 B2 | 2/2009 | Shelton, IV et al. |
| 7,490,749 B2 | 2/2009 | Schall et al. |
| 7,506,790 B2 | 3/2009 | Shelton, IV |
| 7,506,791 B2 | 3/2009 | Omaits et al. |
| 7,513,408 B2 | 4/2009 | Shelton, IV et al. |
| 7,530,484 B1 | 5/2009 | Durrani |
| 7,543,730 B1 | 6/2009 | Marczyk |
| 7,543,731 B2 | 6/2009 | Green et al. |
| 7,546,940 B2 | 6/2009 | Milliman et al. |
| 7,549,564 B2 | 6/2009 | Boudreaux |
| 7,552,854 B2 | 6/2009 | Wixey et al. |
| 7,556,186 B2 | 7/2009 | Milliman |
| 7,565,993 B2 | 7/2009 | Milliman et al. |
| 7,568,604 B2 | 8/2009 | Ehrenfels et al. |
| 7,588,174 B2 | 9/2009 | Holsten et al. |
| 7,588,175 B2 | 9/2009 | Timm et al. |
| 7,588,177 B2 | 9/2009 | Racenet |
| 7,604,151 B2 | 10/2009 | Hess et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,631,793 B2 | 12/2009 | Rethy et al. |
| 7,635,074 B2 | 12/2009 | Olson et al. |
| 7,637,409 B2 | 12/2009 | Marczyk |
| 7,637,410 B2 | 12/2009 | Marczyk |
| 7,641,091 B2 | 1/2010 | Olson et al. |
| 7,641,093 B2 | 1/2010 | Doll et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,781 B2 | 3/2010 | Swayze et al. |
| 7,682,367 B2 | 3/2010 | Shah et al. |

(56) References Cited

U.S. PATENT DOCUMENTS

| | | |
|---|---|---|
| 7,690,547 B2 | 4/2010 | Racenet et al. |
| 7,703,653 B2 | 4/2010 | Shah et al. |
| 7,717,312 B2 | 5/2010 | Beetel |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,721,936 B2 | 5/2010 | Shelton, IV et al. |
| 7,726,538 B2 | 6/2010 | Holsten et al. |
| 7,726,539 B2 | 6/2010 | Holsten et al. |
| 7,731,073 B2 | 6/2010 | Wixey et al. |
| 7,735,703 B2 | 6/2010 | Morgan et al. |
| 7,753,245 B2 | 7/2010 | Boudreaux et al. |
| 7,753,246 B2 | 7/2010 | Scirica |
| 7,757,925 B2 | 7/2010 | Viola et al. |
| 7,766,210 B2 | 8/2010 | Shelton, IV et al. |
| 7,770,774 B2 | 8/2010 | Mastri et al. |
| 7,780,054 B2 | 8/2010 | Wales |
| 7,780,055 B2 | 8/2010 | Scirica et al. |
| 7,784,662 B2 | 8/2010 | Wales et al. |
| 7,784,663 B2 | 8/2010 | Shelton, IV |
| 7,793,812 B2 | 9/2010 | Moore et al. |
| 7,798,386 B2 | 9/2010 | Schall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,819,298 B2 | 10/2010 | Hall et al. |
| 7,819,896 B2 | 10/2010 | Racenet |
| 7,823,760 B2 | 11/2010 | Zemlok et al. |
| 7,828,188 B2 | 11/2010 | Jankowski |
| 7,828,189 B2 | 11/2010 | Holsten et al. |
| 7,837,079 B2 | 11/2010 | Holsten et al. |
| 7,837,081 B2 | 11/2010 | Holsten et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,857,184 B2 | 12/2010 | Viola |
| 7,857,185 B2 | 12/2010 | Swayze et al. |
| 7,857,187 B2 | 12/2010 | Milliman |
| 7,861,906 B2 | 1/2011 | Doll et al. |
| 7,866,525 B2 | 1/2011 | Scirica |
| 7,866,527 B2 | 1/2011 | Hall et al. |
| 7,891,534 B2 | 2/2011 | Wenchell et al. |
| 7,905,381 B2 | 3/2011 | Baxter, III et al. |
| 7,909,220 B2 | 3/2011 | Viola |
| 7,909,221 B2 | 3/2011 | Viola et al. |
| 7,913,891 B2 | 3/2011 | Doll et al. |
| 7,914,543 B2 | 3/2011 | Roth et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,922,063 B2 | 4/2011 | Zemlok et al. |
| 7,934,628 B2 | 5/2011 | Wenchell et al. |
| 7,934,629 B2 | 5/2011 | Wixey et al. |
| 7,934,630 B2 | 5/2011 | Shelton, IV et al. |
| 7,942,300 B2 | 5/2011 | Rethy et al. |
| 7,954,685 B2 | 6/2011 | Viola |
| 7,954,686 B2 | 6/2011 | Baxter, III et al. |
| 7,959,050 B2 | 6/2011 | Smith et al. |
| 7,963,433 B2 | 6/2011 | Whitman et al. |
| 7,992,758 B2 | 8/2011 | Whitman et al. |
| 8,002,795 B2 | 8/2011 | Beetel |
| 8,006,887 B2 | 8/2011 | Marczyk |
| 8,007,513 B2 | 8/2011 | Nalagatla et al. |
| 8,008,598 B2 | 8/2011 | Whitman et al. |
| 8,011,550 B2 | 9/2011 | Aranyi et al. |
| 8,011,553 B2 | 9/2011 | Mastri et al. |
| 8,012,170 B2 | 9/2011 | Whitman et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,885 B2 | 10/2011 | Smith et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,046 B2 | 10/2011 | Smith et al. |
| 8,052,024 B2 | 11/2011 | Viola et al. |
| 8,056,788 B2 | 11/2011 | Mastri et al. |
| 8,056,789 B1 | 11/2011 | White et al. |
| 8,061,576 B2 | 11/2011 | Cappola |
| 8,061,577 B2 | 11/2011 | Racenet et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,070,036 B1 | 12/2011 | Knodel |
| 8,074,861 B2 | 12/2011 | Ehrenfels et al. |
| 8,083,118 B2 | 12/2011 | Milliman et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,092,493 B2 | 1/2012 | Marczyk |
| 8,100,309 B2 | 1/2012 | Marczyk |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,410 B2 | 2/2012 | Hall et al. |
| 8,118,207 B2 | 2/2012 | Racenet et al. |
| 8,123,100 B2 | 2/2012 | Holsten et al. |
| 8,127,976 B2 | 3/2012 | Scirica et al. |
| 8,136,712 B2 | 3/2012 | Zingman |
| 8,152,041 B2 | 4/2012 | Kostrzewski |
| 8,157,145 B2 | 4/2012 | Shelton, IV et al. |
| 8,157,150 B2 | 4/2012 | Viola et al. |
| 8,157,152 B2 | 4/2012 | Holsten et al. |
| 8,181,839 B2 | 5/2012 | Beetel |
| 8,186,555 B2 | 5/2012 | Shelton, IV et al. |
| 8,186,556 B2 | 5/2012 | Viola |
| 8,186,560 B2 | 5/2012 | Hess et al. |
| 8,191,752 B2 | 6/2012 | Scirica |
| 8,196,795 B2 | 6/2012 | Moore et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,411 B2 | 7/2012 | Yates et al. |
| 8,210,416 B2 | 7/2012 | Milliman et al. |
| 8,220,688 B2 | 7/2012 | Laurent et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,274 B2 | 8/2012 | Cappola |
| 8,236,010 B2 | 8/2012 | Shelton et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,256,656 B2 | 9/2012 | Milliman et al. |
| 8,272,552 B2 | 9/2012 | Holsten et al. |
| 8,272,554 B2 | 9/2012 | Whitman et al. |
| 8,281,972 B2 | 10/2012 | Wixey et al. |
| 8,281,973 B2 | 10/2012 | Wenchell et al. |
| 8,286,846 B2 | 10/2012 | Smith et al. |
| 8,292,146 B2 | 10/2012 | Holsten et al. |
| 8,292,148 B2 | 10/2012 | Viola |
| 8,292,151 B2 | 10/2012 | Viola |
| 8,292,152 B2 | 10/2012 | Milliman et al. |
| 8,292,153 B2 | 10/2012 | Jankowski |
| 8,292,157 B2 | 10/2012 | Smith et al. |
| 8,308,041 B2 | 11/2012 | Kostrzewski |
| 8,308,043 B2 | 11/2012 | Bindra et al. |
| 8,317,070 B2 | 11/2012 | Hueil et al. |
| 8,322,455 B2 | 12/2012 | Shelton, IV et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,125 B2 | 1/2013 | Viola et al. |
| 8,348,129 B2 | 1/2013 | Bedi et al. |
| 8,348,131 B2 | 1/2013 | Omaits et al. |
| 8,353,440 B2 | 1/2013 | Whitman et al. |

(56) References Cited

U.S. PATENT DOCUMENTS

| | | |
|---|---|---|
| 8,360,297 B2 | 1/2013 | Shelton, IV et al. |
| 8,360,299 B2 | 1/2013 | Zemlok et al. |
| 8,393,513 B2 | 3/2013 | Jankowski |
| 8,397,972 B2 | 3/2013 | Kostrzewski |
| 8,397,973 B1 | 3/2013 | Hausen |
| 8,403,198 B2 | 3/2013 | Sorrentino et al. |
| 8,413,868 B2 | 4/2013 | Cappola |
| 8,414,577 B2 | 4/2013 | Boudreaux et al. |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,439,246 B1 | 5/2013 | Knodel |
| 8,444,036 B2 | 5/2013 | Shelton, IV |
| 8,453,907 B2 | 6/2013 | Laurent et al. |
| 8,453,912 B2 | 6/2013 | Mastri et al. |
| 8,453,913 B2 | 6/2013 | Milliman |
| 8,459,520 B2 | 6/2013 | Giordano et al. |
| 8,459,522 B2 | 6/2013 | Marczyk |
| 8,464,922 B2 | 6/2013 | Marczyk |
| 8,469,252 B2 | 6/2013 | Holcomb et al. |
| 8,479,967 B2 | 7/2013 | Marczyk |
| 8,496,152 B2 | 7/2013 | Viola |
| 8,496,155 B2 | 7/2013 | Knodel |
| 8,496,156 B2 | 7/2013 | Sniffin et al. |
| 8,496,683 B2 | 7/2013 | Prommersberger et al. |
| 8,505,799 B2 | 8/2013 | Viola et al. |
| 8,505,801 B2 | 8/2013 | Ehrenfels et al. |
| 8,517,239 B2 | 8/2013 | Scheib et al. |
| 8,517,240 B1 | 8/2013 | Mata et al. |
| 8,523,043 B2 | 9/2013 | Ullrich et al. |
| 8,540,130 B2 | 9/2013 | Moore et al. |
| 8,540,133 B2 | 9/2013 | Bedi et al. |
| 8,540,625 B2 | 9/2013 | Miyoshi |
| 8,544,712 B2 | 10/2013 | Jankowski |
| 8,556,151 B2 | 10/2013 | Viola |
| 8,556,152 B2 | 10/2013 | Marczyk et al. |
| 8,556,153 B1 | 10/2013 | Knodel |
| 8,561,871 B2 | 10/2013 | Rajappa et al. |
| 8,561,874 B2 | 10/2013 | Scirica |
| 8,573,459 B2 | 11/2013 | Smith et al. |
| 8,573,460 B2 | 11/2013 | Cappola |
| 8,573,462 B2 | 11/2013 | Smith et al. |
| 8,573,463 B2 | 11/2013 | Scirica et al. |
| 8,573,464 B2 | 11/2013 | Nalagatla et al. |
| 8,579,176 B2 | 11/2013 | Smith et al. |
| 8,579,177 B2 | 11/2013 | Beetel |
| 8,584,919 B2 | 11/2013 | Hueil et al. |
| 8,584,921 B2 | 11/2013 | Scirica |
| 8,596,513 B2 | 12/2013 | Olson |
| 8,608,043 B2 | 12/2013 | Scirica |
| 8,608,045 B2 | 12/2013 | Smith et al. |
| 8,616,427 B2 | 12/2013 | Viola |
| 8,622,274 B2 | 1/2014 | Yates et al. |
| 8,627,992 B2 | 1/2014 | Edoga et al. |
| 8,627,993 B2 | 1/2014 | Smith et al. |
| 8,627,995 B2 | 1/2014 | Smith et al. |
| 8,631,990 B1 | 1/2014 | Park et al. |
| 8,632,525 B2 | 1/2014 | Kerr et al. |
| 8,632,535 B2 | 1/2014 | Shelton, IV et al. |
| 8,636,189 B1 | 1/2014 | Knodel et al. |
| 8,636,190 B2 | 1/2014 | Zemlok et al. |
| 8,636,192 B2 | 1/2014 | Farascioni et al. |
| 8,636,193 B2 | 1/2014 | Whitman et al. |
| 8,636,762 B2 | 1/2014 | Whitman et al. |
| 8,636,766 B2 | 1/2014 | Milliman et al. |
| 8,657,174 B2 | 2/2014 | Yates et al. |
| 8,657,176 B2 | 2/2014 | Shelton, IV et al. |
| 8,657,178 B2 | 2/2014 | Hueil et al. |
| 8,672,209 B2 | 3/2014 | Crainich |
| 8,672,951 B2 | 3/2014 | Smith et al. |
| 8,685,004 B2 | 4/2014 | Zemlock et al. |
| 8,695,865 B2 | 4/2014 | Smith et al. |
| 8,696,665 B2 | 4/2014 | Hunt et al. |
| 8,708,211 B2 | 4/2014 | Zemlok et al. |
| 8,708,213 B2 | 4/2014 | Shelton, IV et al. |
| 8,740,034 B2 | 6/2014 | Morgan et al. |
| 8,740,035 B2 | 6/2014 | Mastri et al. |
| 8,740,036 B2 | 6/2014 | Williams |
| 8,752,748 B2 | 6/2014 | Whitman et al. |
| 8,763,876 B2 | 7/2014 | Kostrzewski |
| 8,770,458 B2 | 7/2014 | Scirica |
| 8,770,459 B2 | 7/2014 | Racenet et al. |
| 8,789,741 B2 | 7/2014 | Baxter, III et al. |
| 8,800,839 B2 | 8/2014 | Beetel |
| 8,800,840 B2 | 8/2014 | Jankowski |
| 8,800,841 B2 | 8/2014 | Ellerhorst et al. |
| 8,806,973 B2 | 8/2014 | Ross et al. |
| 8,807,414 B2 | 8/2014 | Ross et al. |
| 8,820,603 B2 | 9/2014 | Shelton, IV et al. |
| 8,820,608 B2 | 9/2014 | Miyamoto |
| 8,833,631 B2 | 9/2014 | Munro, III et al. |
| 8,840,003 B2 | 9/2014 | Morgan et al. |
| 8,858,571 B2 | 10/2014 | Shelton, IV et al. |
| 8,875,971 B2 | 11/2014 | Hall et al. |
| 8,875,972 B2 | 11/2014 | Weisenburgh, II et al. |
| 8,887,979 B2 | 11/2014 | Mastri et al. |
| 8,899,462 B2 | 12/2014 | Kostrzewski et al. |
| 8,899,463 B2 | 12/2014 | Schall et al. |
| 8,905,288 B2 | 12/2014 | Wenchell |
| 8,920,435 B2 | 12/2014 | Smith et al. |
| 8,925,783 B2 | 1/2015 | Zernlok et al. |
| 8,931,679 B2 | 1/2015 | Kostrzewski |
| 8,931,683 B2 | 1/2015 | Racenet et al. |
| 8,939,343 B2 | 1/2015 | Milliman et al. |
| 8,967,444 B2 | 3/2015 | Beetel |
| 8,967,446 B2 | 3/2015 | Beardsley et al. |
| 8,967,447 B2 | 3/2015 | Hartoumbekis |
| 8,968,276 B2 | 3/2015 | Zemlok et al. |
| 8,973,803 B2 | 3/2015 | Hall et al. |
| 8,979,827 B2 | 3/2015 | Cappola |
| 9,004,340 B2 | 4/2015 | Scirica |
| 9,010,611 B2 | 4/2015 | Ross et al. |
| 9,016,541 B2 | 4/2015 | Viola et al. |
| 9,016,545 B2 | 4/2015 | Aranyi et al. |
| 9,022,271 B2 | 5/2015 | Scirica |
| 9,023,014 B2 | 5/2015 | Chowaniec et al. |
| 9,027,817 B2 | 5/2015 | Milliman et al. |
| 9,027,818 B2 | 5/2015 | Scirica et al. |
| 9,033,202 B2 | 5/2015 | Scirica |
| 9,038,880 B1 | 5/2015 | Donohoe |
| 9,055,943 B2 | 6/2015 | Zemlok et al. |
| 9,072,515 B2 | 7/2015 | Hall et al. |
| 9,084,601 B2 | 7/2015 | Moore et al. |
| 9,101,358 B2 | 8/2015 | Kerr et al. |
| 9,204,876 B2 | 12/2015 | Cappola et al. |
| 9,237,890 B2 | 1/2016 | Kostrzewski |
| 9,265,585 B2 | 2/2016 | Wingardner et al. |
| 9,282,966 B2 | 3/2016 | Shelton, IV et al. |
| 9,386,984 B2 | 7/2016 | Aronhalt et al. |
| 9,402,629 B2 | 8/2016 | Ehrenfels et al. |
| 9,510,830 B2 | 12/2016 | Shelton, IV et al. |
| 9,532,782 B2 | 1/2017 | Kostrzewski |
| 9,662,108 B2 | 5/2017 | Williams |
| 9,737,302 B2 | 8/2017 | Shelton, IV et al. |
| 9,737,303 B2 | 8/2017 | Shelton, IV et al. |
| 9,797,486 B2 | 10/2017 | Zergiebel et al. |
| 2002/0025243 A1 | 2/2002 | Heck |
| 2002/0029044 A1 | 3/2002 | Monassevitch et al. |
| 2002/0062136 A1 | 5/2002 | Hillstead |
| 2002/0120279 A1 | 8/2002 | Deguillebon et al. |
| 2003/0130677 A1 | 7/2003 | Whitman et al. |
| 2004/0006372 A1 | 1/2004 | Racenet et al. |
| 2004/0138705 A1 | 7/2004 | Heino et al. |
| 2005/0234478 A1 | 10/2005 | Wixey |
| 2006/0097026 A1 | 5/2006 | Shelton, IV |
| 2006/0100644 A1 | 5/2006 | Viola |
| 2006/0180634 A1 | 8/2006 | Shelton, IV et al. |
| 2006/0235442 A1 | 10/2006 | Huitema |
| 2006/0289602 A1 | 12/2006 | Wales et al. |
| 2007/0034664 A1 | 2/2007 | Jiang |
| 2007/0039997 A1 | 2/2007 | Mather et al. |
| 2007/0057014 A1 | 3/2007 | Whitman et al. |
| 2007/0068990 A1 | 3/2007 | Shelton, IV |

(56) References Cited

U.S. PATENT DOCUMENTS

| | | |
|---|---|---|
| 2007/0084897 A1 | 4/2007 | Shelton, IV et al. |
| 2007/0102472 A1 | 5/2007 | Shelton, IV |
| 2007/0119901 A1 | 5/2007 | Ehrenfels et al. |
| 2007/0131732 A1 | 6/2007 | Holsten et al. |
| 2007/0175950 A1 | 8/2007 | Shelton, IV et al. |
| 2007/0175951 A1 | 8/2007 | Shelton, IV et al. |
| 2008/0029574 A1 | 2/2008 | Shelton et al. |
| 2008/0029575 A1 | 2/2008 | Shelton et al. |
| 2008/0041918 A1 | 2/2008 | Holsten et al. |
| 2008/0078807 A1 | 4/2008 | Hess et al. |
| 2008/0083807 A1 | 4/2008 | Beardsley et al. |
| 2008/0169333 A1 | 7/2008 | Shelton et al. |
| 2008/0179375 A1 | 7/2008 | Scirica |
| 2008/0255607 A1 | 10/2008 | Zemick |
| 2009/0001129 A1 | 1/2009 | Marczyk |
| 2009/0001130 A1 | 1/2009 | Hess et al. |
| 2009/0026245 A1 | 1/2009 | Holsten et al. |
| 2009/0048589 A1 | 2/2009 | Takashino et al. |
| 2009/0057369 A1 | 3/2009 | Smith et al. |
| 2009/0090763 A1 | 4/2009 | Zemlok et al. |
| 2009/0145947 A1* | 6/2009 | Scirica ............... A61B 17/0686 227/176.1 |
| 2009/0198272 A1 | 8/2009 | Kerver et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0277948 A1 | 11/2009 | Beardsley et al. |
| 2009/0277949 A1 | 11/2009 | Viola et al. |
| 2010/0069942 A1 | 3/2010 | Shelton, IV |
| 2010/0072258 A1 | 3/2010 | Farascioni et al. |
| 2010/0089970 A1 | 4/2010 | Smith et al. |
| 2010/0193566 A1 | 8/2010 | Scheib et al. |
| 2010/0230465 A1 | 9/2010 | Smith et al. |
| 2010/0331820 A1 | 12/2010 | Prisco et al. |
| 2011/0036892 A1 | 2/2011 | Marczyk et al. |
| 2011/0042440 A1 | 2/2011 | Holsten et al. |
| 2011/0087276 A1 | 4/2011 | Bedi et al. |
| 2011/0108601 A1 | 5/2011 | Clark et al. |
| 2011/0108603 A1 | 5/2011 | Racenet et al. |
| 2011/0121049 A1 | 5/2011 | Malinouskas et al. |
| 2011/0125138 A1 | 5/2011 | Malinouskas et al. |
| 2011/0127185 A1 | 6/2011 | Ward |
| 2011/0139852 A1 | 6/2011 | Zingman |
| 2011/0147433 A1 | 6/2011 | Shelton, IV et al. |
| 2011/0155784 A1 | 6/2011 | Shelton, IV et al. |
| 2011/0155787 A1 | 6/2011 | Baxter, III et al. |
| 2011/0290851 A1 | 12/2011 | Shelton, IV et al. |
| 2011/0290853 A1 | 12/2011 | Shelton, IV et al. |
| 2012/0061446 A1 | 3/2012 | Knodel et al. |
| 2012/0074198 A1 | 3/2012 | Hultema et al. |
| 2012/0074200 A1 | 3/2012 | Schmid et al. |
| 2012/0078243 A1 | 3/2012 | Worrell et al. |
| 2012/0080482 A1 | 4/2012 | Schall et al. |
| 2012/0080498 A1 | 4/2012 | Shelton, IV et al. |
| 2012/0091182 A1 | 4/2012 | Marczyk |
| 2012/0109186 A1 | 5/2012 | Parrott et al. |
| 2012/0168487 A1 | 7/2012 | Holsten et al. |
| 2012/0193396 A1 | 8/2012 | Zemlok et al. |
| 2012/0211542 A1 | 8/2012 | Racenet |
| 2012/0253298 A1 | 10/2012 | Henderson et al. |
| 2012/0286022 A1 | 11/2012 | Olson et al. |
| 2012/0318844 A1* | 12/2012 | Shelton, IV ..... A61B 17/00234 227/176.1 |
| 2012/0325893 A1 | 12/2012 | Pastorelli et al. |
| 2013/0001270 A1 | 1/2013 | Kostrzewski |
| 2013/0015229 A1 | 1/2013 | Viola |
| 2013/0015230 A1 | 1/2013 | Wixey |
| 2013/0015232 A1 | 1/2013 | Smith et al. |
| 2013/0015233 A1 | 1/2013 | Viola |
| 2013/0020375 A1 | 1/2013 | Shelton, IV et al. |
| 2013/0037595 A1 | 2/2013 | Gupta et al. |
| 2013/0048697 A1 | 2/2013 | Shelton, IV et al. |
| 2013/0056521 A1 | 3/2013 | Swensgard |
| 2013/0079814 A1 | 3/2013 | Hess et al. |
| 2013/0087603 A1 | 4/2013 | Viola |
| 2013/0092717 A1 | 4/2013 | Marczyk et al. |
| 2013/0098964 A1 | 4/2013 | Smith et al. |
| 2013/0098965 A1 | 4/2013 | Kostrzewski et al. |
| 2013/0098969 A1 | 4/2013 | Scirica et al. |
| 2013/0105545 A1 | 5/2013 | Burbank |
| 2013/0105547 A1 | 5/2013 | Beardsley |
| 2013/0105548 A1 | 5/2013 | Hodgkinson et al. |
| 2013/0105549 A1 | 5/2013 | Holsten et al. |
| 2013/0112730 A1 | 5/2013 | Whitman et al. |
| 2013/0112731 A1 | 5/2013 | Hodgkinson |
| 2013/0126583 A1 | 5/2013 | Hueil et al. |
| 2013/0126586 A1 | 5/2013 | Zhang et al. |
| 2013/0146640 A1 | 6/2013 | Jankowski |
| 2013/0172928 A1 | 7/2013 | Kostrzewski |
| 2013/0172929 A1 | 7/2013 | Hess et al. |
| 2013/0175317 A1 | 7/2013 | Yates et al. |
| 2013/0175322 A1 | 7/2013 | Yates et al. |
| 2013/0184718 A1 | 7/2013 | Smith et al. |
| 2013/0186931 A1 | 7/2013 | Beardsley |
| 2013/0186932 A1 | 7/2013 | Shelton, IV et al. |
| 2013/0186933 A1 | 7/2013 | Shelton, IV et al. |
| 2013/0193188 A1 | 8/2013 | Shelton, IV et al. |
| 2013/0200132 A1 | 8/2013 | Moore et al. |
| 2013/0206816 A1 | 8/2013 | Penna |
| 2013/0214025 A1 | 8/2013 | Zemlok et al. |
| 2013/0221065 A1 | 8/2013 | Aronhalt et al. |
| 2013/0240604 A1 | 9/2013 | Knodel |
| 2013/0248582 A1 | 9/2013 | Scirica |
| 2013/0256370 A1 | 10/2013 | Smith et al. |
| 2013/0256371 A1 | 10/2013 | Shelton, IV |
| 2013/0270321 A1 | 10/2013 | Marczyk |
| 2013/0270323 A1 | 10/2013 | Marczyk |
| 2013/0284789 A1 | 10/2013 | Smith et al. |
| 2013/0284791 A1 | 10/2013 | Olson et al. |
| 2013/0299552 A1 | 11/2013 | Viola |
| 2013/0306702 A1 | 11/2013 | Viola et al. |
| 2013/0306703 A1 | 11/2013 | Ehrenfels et al. |
| 2013/0306706 A1 | 11/2013 | Knodel |
| 2013/0313303 A1 | 11/2013 | Shelton, IV et al. |
| 2013/0327809 A1 | 12/2013 | Shelton, IV et al. |
| 2013/0327810 A1 | 12/2013 | Swayze et al. |
| 2013/0334278 A1 | 12/2013 | Kerr et al. |
| 2013/0334280 A1 | 12/2013 | Krehel et al. |
| 2013/0334281 A1 | 12/2013 | Williams |
| 2013/0334283 A1 | 12/2013 | Swayze et al. |
| 2013/0334284 A1 | 12/2013 | Swayze et al. |
| 2013/0334285 A1 | 12/2013 | Swayze et al. |
| 2013/0334286 A1 | 12/2013 | Swayze et al. |
| 2013/0334287 A1 | 12/2013 | Shelton, IV |
| 2013/0334288 A1 | 12/2013 | Shelton, IV |
| 2014/0014704 A1 | 1/2014 | Onukuri et al. |
| 2014/0014707 A1 | 1/2014 | Onukuri et al. |
| 2014/0021239 A1 | 1/2014 | Kostrzewski |
| 2014/0025046 A1 | 1/2014 | Williams et al. |
| 2014/0027491 A1 | 1/2014 | Beardsley et al. |
| 2014/0027493 A1 | 1/2014 | Jankowski |
| 2014/0042204 A1 | 2/2014 | Beetel |
| 2014/0103092 A1 | 4/2014 | Kostrzewski et al. |
| 2014/0103093 A1 | 4/2014 | Koch, Jr. et al. |
| 2014/0107640 A1 | 4/2014 | Yates et al. |
| 2014/0110453 A1 | 4/2014 | Wingardner et al. |
| 2014/0131416 A1 | 5/2014 | Whitman et al. |
| 2014/0135832 A1 | 5/2014 | Park et al. |
| 2014/0151433 A1 | 6/2014 | Shelton, IV et al. |
| 2014/0151434 A1 | 6/2014 | Shelton, IV et al. |
| 2014/0158746 A1 | 6/2014 | Mastri et al. |
| 2014/0166727 A1 | 6/2014 | Swayze et al. |
| 2014/0175146 A1 | 6/2014 | Knodel |
| 2014/0175149 A1 | 6/2014 | Smith et al. |
| 2014/0203063 A1 | 7/2014 | Hessler et al. |
| 2014/0205637 A1 | 7/2014 | Widenhouse et al. |
| 2014/0224856 A1 | 8/2014 | Smith et al. |
| 2014/0236173 A1 | 8/2014 | Scirica et al. |
| 2014/0236184 A1 | 8/2014 | Leimbach |
| 2014/0239038 A1 | 8/2014 | Leimbach et al. |
| 2014/0239041 A1 | 8/2014 | Zerkle et al. |
| 2014/0239044 A1 | 8/2014 | Hoffman |
| 2014/0246474 A1 | 9/2014 | Hall et al. |
| 2014/0246475 A1 | 9/2014 | Hall et al. |

(56) References Cited

U.S. PATENT DOCUMENTS

| | | |
|---|---|---|
| 2014/0246478 A1 | 9/2014 | Baber et al. |
| 2014/0246479 A1 | 9/2014 | Baber et al. |
| 2014/0260746 A1 | 9/2014 | Sakaguchi et al. |
| 2014/0263537 A1 | 9/2014 | Leimbach et al. |
| 2014/0263539 A1 | 9/2014 | Leimbach et al. |
| 2014/0263541 A1 | 9/2014 | Leimbach et al. |
| 2014/0263542 A1 | 9/2014 | Leimbach et al. |
| 2014/0263543 A1 | 9/2014 | Leimbach et al. |
| 2014/0263545 A1 | 9/2014 | Williams et al. |
| 2014/0263546 A1 | 9/2014 | Aranyi |
| 2014/0263550 A1 | 9/2014 | Aranyi et al. |
| 2014/0263553 A1 | 9/2014 | Leimbach et al. |
| 2014/0263554 A1 | 9/2014 | Leimbach et al. |
| 2014/0263555 A1 | 9/2014 | Hufnagel et al. |
| 2014/0263559 A1 | 9/2014 | Williams et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263566 A1 | 9/2014 | Williams et al. |
| 2014/0263567 A1 | 9/2014 | Williams et al. |
| 2014/0263568 A1 | 9/2014 | Williams et al. |
| 2014/0263569 A1 | 9/2014 | Williams et al. |
| 2014/0263570 A1 | 9/2014 | Hopkins et al. |
| 2014/0263571 A1 | 9/2014 | Morgan et al. |
| 2014/0263572 A1 | 9/2014 | Shelton, IV et al. |
| 2014/0284372 A1 | 9/2014 | Kostrzewski |
| 2014/0291378 A1 | 10/2014 | Shelton, IV et al. |
| 2014/0299649 A1 | 10/2014 | Shelton, IV et al. |
| 2014/0305986 A1 | 10/2014 | Hall et al. |
| 2014/0305988 A1 | 10/2014 | Boudreaux et al. |
| 2014/0305992 A1 | 10/2014 | Kimsey et al. |
| 2014/0305994 A1 | 10/2014 | Parihar et al. |
| 2014/0353359 A1 | 12/2014 | Hall et al. |
| 2015/0008248 A1 | 1/2015 | Giordano et al. |
| 2015/0034697 A1 | 2/2015 | Mastri et al. |
| 2015/0041518 A1 | 2/2015 | Shelton, IV et al. |
| 2015/0053738 A1 | 2/2015 | Morgan et al. |
| 2015/0053740 A1 | 2/2015 | Shelton, IV |
| 2015/0053741 A1 | 2/2015 | Shelton, IV et al. |
| 2015/0053742 A1 | 2/2015 | Shelton, IV et al. |
| 2015/0053743 A1 | 2/2015 | Yates et al. |
| 2015/0053744 A1 | 2/2015 | Swayze et al. |
| 2015/0053745 A1 | 2/2015 | Yates et al. |
| 2015/0053746 A1 | 2/2015 | Shelton, IV et al. |
| 2015/0053748 A1 | 2/2015 | Yates et al. |
| 2015/0053749 A1 | 2/2015 | Shelton, IV et al. |
| 2015/0054753 A1 | 2/2015 | Morgan et al. |
| 2015/0060516 A1 | 3/2015 | Collings et al. |
| 2015/0060517 A1 | 3/2015 | Williams |
| 2015/0060521 A1 | 3/2015 | Weisenburgh, II et al. |
| 2015/0076205 A1 | 3/2015 | Zergiebel |
| 2015/0076206 A1 | 3/2015 | Sapre |
| 2015/0076209 A1 | 3/2015 | Shelton, IV et al. |
| 2015/0076210 A1 | 3/2015 | Shelton, IV et al. |
| 2015/0076212 A1 | 3/2015 | Shelton, IV |
| 2015/0083781 A1 | 3/2015 | Giordano et al. |
| 2015/0083783 A1 | 3/2015 | Shelton, IV et al. |
| 2015/0090760 A1 | 4/2015 | Giordano et al. |
| 2015/0090761 A1 | 4/2015 | Giordano et al. |
| 2015/0090762 A1 | 4/2015 | Giordano et al. |
| 2015/0090764 A1 | 4/2015 | Zemlok et al. |
| 2015/0108201 A1 | 4/2015 | Williams |
| 2015/0122872 A1 | 5/2015 | Olson et al. |
| 2015/0127046 A1 | 5/2015 | Peterson |
| 2015/0129631 A1 | 5/2015 | Beetel |
| 2015/0129634 A1 | 5/2015 | Shelton, IV et al. |
| 2015/0133995 A1 | 5/2015 | Shelton, IV et al. |
| 2015/0133996 A1 | 5/2015 | Shelton, IV et al. |
| 2015/0134076 A1 | 5/2015 | Shelton, IV et al. |
| 2015/0144678 A1 | 5/2015 | Hall et al. |
| 2015/0201935 A1 | 7/2015 | Weisenburgh, II et al. |
| 2015/0208902 A1 | 7/2015 | Okamoto |
| 2015/0245834 A1 | 9/2015 | Scirica et al. |
| 2015/0272576 A1 | 10/2015 | Cappola |
| 2015/0289873 A1 | 10/2015 | Shelton, IV et al. |
| 2015/0297221 A1 | 10/2015 | Kerr et al. |
| 2015/0297233 A1 | 10/2015 | Huitema et al. |
| 2015/0380187 A1 | 12/2015 | Zergiebel et al. |
| 2016/0000439 A1 | 1/2016 | Weisenburgh, II et al. |
| 2016/0000440 A1 | 1/2016 | Weisenburgh, II et al. |
| 2016/0058447 A1 | 3/2016 | Posada et al. |
| 2016/0183948 A1 | 6/2016 | Shelton, IV et al. |
| 2016/0338702 A1 | 11/2016 | Ehrenfels et al. |
| 2016/0374672 A1 | 12/2016 | Bear et al. |
| 2016/0374675 A1 | 12/2016 | Shelton, IV et al. |
| 2017/0007241 A1 | 1/2017 | Shelton, IV et al. |
| 2017/0007242 A1 | 1/2017 | Shelton, IV et al. |
| 2017/0007243 A1 | 1/2017 | Shelton, IV et al. |
| 2017/0007249 A1 | 1/2017 | Shelton, IV et al. |
| 2017/0231633 A1 | 8/2017 | Marczyk et al. |
| 2017/0245856 A1 | 8/2017 | Baxter, III et al. |
| 2017/0245858 A1 | 8/2017 | Williams |
| 2017/0281161 A1 | 10/2017 | Shelton, IV et al. |
| 2017/0281165 A1 | 10/2017 | Harris et al. |
| 2017/0281168 A1 | 10/2017 | Shelton, IV et al. |
| 2017/0290583 A1 | 10/2017 | Reed et al. |
| 2017/0290584 A1 | 10/2017 | Jasemian et al. |

FOREIGN PATENT DOCUMENTS

| | | |
|---|---|---|
| EP | 0 514 139 A2 | 11/1992 |
| EP | 0 536 903 A2 | 4/1993 |
| EP | 0 596 543 A1 | 5/1994 |
| EP | 1 523 944 A1 | 4/2005 |
| EP | 1 759 812 A1 | 3/2007 |
| EP | 1 915 953 A1 | 4/2008 |
| EP | 1 479 348 B1 | 7/2008 |
| EP | 2 044 893 A2 | 9/2008 |
| EP | 2 005 902 A2 | 12/2008 |
| EP | 2 090 241 A1 | 8/2009 |
| EP | 2 263 568 A2 | 12/2010 |
| EP | 2 361 562 A1 | 8/2011 |
| EP | 2 462 875 A2 | 6/2012 |
| EP | 2 486 859 A2 | 8/2012 |
| EP | 2 764 833 A2 | 8/2014 |
| EP | 2 772 192 A1 | 9/2014 |
| EP | 2 777 530 A1 | 9/2014 |
| EP | 2 815 705 A1 | 12/2014 |
| EP | 2 923 661 A2 | 3/2015 |
| EP | 2 853 204 A1 | 4/2015 |
| EP | 2 891 462 A1 | 7/2015 |
| EP | 2 926 742 A1 | 10/2015 |
| EP | 2 942 020 A2 | 11/2015 |
| EP | 2 959 851 A1 | 12/2015 |
| EP | 3 135 225 A2 | 3/2017 |
| EP | 3 238 639 A2 | 3/2017 |
| EP | 3 338 653 A1 | 6/2018 |
| EP | 3 338 698 A1 | 6/2018 |
| EP | 3 338 702 A1 | 6/2018 |
| JP | 2001-087272 A | 4/2001 |
| RU | 2063710 | 7/1996 |
| WO | WO 83/02247 A1 | 7/1983 |
| WO | WO 94/24947 A1 | 11/1994 |
| WO | WO 02/30296 A2 | 4/2002 |
| WO | WO 02/096327 A2 | 12/2002 |
| WO | WO 2003/094747 A1 | 11/2003 |
| WO | WO 2004/032762 A1 | 4/2004 |
| WO | WO 2012/052729 A1 | 4/2012 |
| WO | WO 2014/139440 A1 | 9/2014 |

OTHER PUBLICATIONS

JustRight Surgical, JustRight Surgery, Dec. 31, 2014.

International Searching Authority/US, The International Search Report and the Written Opinion of the International Searching Authority for International Application No. PCT/US2014/028811, titled Surgical Stapler Having Actuation Mechanism with Rotatable Shaft, mailed Aug. 5, 2014.

The International Bureau of WIPO, International Preliminary Report on Patentability, dated Sep. 15, 2015, for International Application No. PCT/US2014/028811.

(56) References Cited

OTHER PUBLICATIONS

European Patent Office, European Search Report for European Application No. EP 14764812.5, entitled "Surgical Stapler Having Actuation Mechanism With Rotatable Shaft," dated Apr. 6, 2017, 6 pgs.

International Searching Authority/ EPO, Invitation to Pay Additional Fees and Communication Relating to the Results of the Partial International Search for PCT/US2017/027269, entitled "Reload Shaft Assembly for Surgical Stapler," dated Jun. 28, 2017, 15 pgs.

International Searching Authority/ EPO, Invitation to Pay Additional Fees and Communication Relating to the Results of the Partial International Search for PCT/US2017/027213, entitled "Surgical Stapler Having a Powered Handle," dated Jul. 5, 2017, 11 pgs.

International Searching Authority/ EPO, Invitation to Pay Additional Fees and Communication Relating to the Results of the Partial International Search for PCT/US2017/027142, entitled "Surgical Stapler Having Articulation Mechanism," dated Jul. 10, 2017, 15 pgs.

European Patent Office, The International Search Report and the Written Opinion of the International Searching Authority for International Application No. PCT/US2017/027269, entitled "Reload Shaft Assembly for Surgical Stapler," mailed Sep. 12, 2017, 22 pgs.

European Patent Office, The International Search Report and the Written Opinion of the International Searching Authority for International Application No. PCT/US2017/027213, entitled "Surgical Stapler Having a Powered Handle," mailed Sep. 13, 2017, 17 pgs.

European Patent Office, The International Search Report and the Written Opinion of the International Searching Authority for International Application No. PCT/US2017/027142, entitled "Surgical Stapler Having Articulation Mechanism," mailed Sep. 14, 2017, 21 pgs.

European Patent Office, The International Search Report and Written Opinion of the International Searching Authority for International Application No. PCT/US2016/045993 titled "Surgical Stapler Having Locking Articulation Joint", mailed Jan. 24, 2017, 20 pgs.

The International Bureau of WIPO, International Preliminary Report on Patentability, for International Application No. PCT/US2016/045993, entitled "Surgical Stapler Having Locking Articulation Joint," dated Feb. 15, 2018, 13 pgs.

European Patent Office, European Search Report for European Application No. 07784007.2, entitled "Surgical Stapler," dated Jun. 15, 2012, 6 pgs.

International Searching Authority, U.S., The International Search Report and the Written Opinion of the International Searching authority for international application PCT/US2014/027768, titled "Surgical Stapler with Expandable Jaw", mailed Jul. 25, 2014, 17 pgs.

European Patent Office, International Search Report and Written Opinion for International Application No. PCT/US2014/028211, entitled "Surgical Stapler with Partial Pockets," mailed Sep. 8, 2014, 17 pgs.

International Searching Authority, U.S., The International Search Report and the Written Opinion of the International Searching authority for international application PCT/US2015/0035379, titled "Surgical Stapler with Circumferential Firing", mailed Sep. 15, 2015, 22 pgs.

The International Bureau of WIPO, International Preliminary Report on Patentability, for International Application No. PCT/US2014/027768, entitled "Surgical Stapler with Expandable Jaw," dated Sep. 24, 2015, 9 pgs.

The International Bureau of WIPO, International Preliminary Report on Patentability for International Application No. PCT/US2015/035379, entitled "Surgical Stapler with Circumferential Firing," dated Dec. 22, 2016, 14 pgs.

European Patent Office, International Search Report and Written Opinion for International Application No. PCT/US2015/050103 titled "Surgical Stapler with Self-Adjusting Staple Height" dated Feb. 17, 2016, 18 pgs.

The International Bureau of WIPO, International Preliminary Report on Patentabilityfor International Application No. PCT/US2015/050103, titled "Surgical Stapler With Self-Adjusting Staple Height," dated Mar. 30, 2017, 12 pgs.

European Patent Office, Partial European Search Report for European Application No. EP 14762896.0, entitled "Surgical Stapler with Expandable Jaw," dated Apr. 10, 2017, 6 pgs.

European Patent Office, Extended European Search Report for European Application No. EP 18186558.5, entitled "Surgical Stapler with Partial Pockets," dated Oct. 10, 2018, 9 pgs.

The International Bureau of WIPO, International Preliminary Report on Patentability, for International Application No. PCT/US2017/027142, entitled "Surgical Stapler Having Articulation Mechanism," dated Oct. 25, 2018, 12 pgs.

The International Bureau of WIPO, International Preliminary Report on Patentability, for International Application No. PCT/US2017/027213, entitled "Surgical Stapler Having Powered Handle," dated Oct. 25, 2018, 9 pgs.

The International Bureau of WIPO, International Preliminary Report on Patentability,for International Application No. PCT/US2017/027269, entitled "Reload Shaft Assembly for Surgical Stapler," dated Oct. 25, 2018, 12 pgs.

European Patent Office, Extended European Search Report for European ApplicationNo. EP 18189960.0, entitled "Surgical Stapler with Expandable Jaw," dated Dec. 13, 2018, 6 pgs.

International Searching Authority/ EPO, Invitation to Pay Additional Fees and Communication Relating to the Results of the Partial International Search for PCT/US2019/019867, entitled "Surgical Stapler Having a Powered Handle," dated May 24, 2019, 19 pgs.

European Patent Office, The International Search Report and the Written Opinion of the International Searching Authority for International Application No. PCT/US2019/019867, entitled "Surgical Stapler Having a Powered Handle," mailed Jul. 19, 2019, 24 pgs.

European Patent Office, Extended European Search Report for European ApplicationNo. EP 19150575.9, entitled "Surgical Stapler Having Actuation Mechanism with Rotatable Shaft," dated Aug. 21, 2019, 5 pgs.

European Patent Office, Extended European Search Report for European ApplicationNo. EP 19180055.6, entitled "Surgical Stapler with Circumferential Firing," dated Sep. 20, 2019, 8 pgs.

European Patent Office, Extended European Search Report for European Application No. EP 20157713.7, entitled "Surgical Stapler with Expandable Jaw," dated May 11, 2020, 6 pgs.

International Searching Authority/ EPO, Invitation to Pay Additional Fees forPCTUS2020/025496, entitled "Reload Cover for Surgical Stapling System," dated Jun. 18, 2019, 15 pgs.

European Patent Office, The International Search Report and the Written Opinion of the International Searching Authority for International Application No. PCT/US2020/019938, entitled "Surgical Stapling Instrument Having a Two-Position Mechanism," mailed Jun. 18, 2020, 16 pgs.

European Patent Office, Extended European Search Report for European ApplicationNo. EP 20161294.2, entitled "Surgical Stapler with Self-Adjusting Staple Height," dated Jun. 22, 2020, 6 pgs.

European Patent Office, The International Search Report and the Written Opinion of the International Searching Authority for International Application No. PCT/US2020/025496, entitled "Reload Cover for Surgical Stapling System," mailed Aug. 13, 2020, 20 pgs.

European Patent Office, Extended European Search Report for European ApplicationNo. EP 22196603.9, entitled "Surgical Stapler with Expandable Jaw," dated Dec. 14, 2022, 6 pgs.

European Patent Office, Extended European Search Report for European ApplicationNo. EP 22203464.7, entitled "Surgical Stapler with Partial Pockets," dated Dec. 20, 2022, 9 pgs.

European Patent Office, Extended European Search Report for European ApplicationNo. EP 22203599.0, entitled "Surgical Stapler Having a Powered Handle," dated Feb. 7, 2023, 7 pgs.

The International Bureau of WIPO, International Preliminary Report on Patentability, for International Application No. PCT/US2021/057231, entitled "Material Combinations and Processing Methods for a Surgical Instrument," dated May 11, 2023, 10 pgs.

The International Bureau of WIPO, International Preliminary Report on Patentability,for International Application No. PCT/US2021/

(56) References Cited

OTHER PUBLICATIONS 057278, entitled "Actuation Shaft Retention Mechanism for Surgical Stapler," dated May 11, 2023, 10 pgs.
The International Bureau of WIPO, International Preliminary Report on Patentability,for International Application No. PCT/US2021/057365, entitled "Surgical Stapler Having a Powered Handle," dated May 11, 2023, 14 pgs.
The International Bureau of WIPO, International Preliminary Report on Patentability,for International Application No. PCT/US2022/012452, entitled "Surgical Stapler Having Shaft Recognition Mechanism," dated Jul. 27, 2023, 8 pgs.
European Patent Office, Extended European Search Report for European ApplicationNo. EP 23185918.2, entitled "Surgical Stapler Having Actuation Mechanism with Rotatable Shaft," dated Sep. 22, 2023, 5 pgs.
European Patent Office, Extended European Search Report for European ApplicationNo. EP 23198045.9, entitled "Reload Shaft Assembly for Surgical Stapler," dated Oct. 25, 2023, 12 pgs.

\* cited by examiner

SURGICAL STAPLER HANDLE ASSEMBLY HAVING ACTUATION MECHANISM WITH LONGITUDINALLY ROTATABLE SHAFT

CROSS REFERENCE TO RELATED APPLICATIONS

This application is a continuation of U.S. patent application Ser. No. 17/980,395 entitled "SURGICAL STAPLER HANDLE ASSEMBLY HAVING ACTUATION MECHANISM WITH LONGITUDINALLY ROTATABLE SHAFT" filed on Nov. 3, 2022, which is a continuation of U.S. patent application Ser. No. 17/141,050 entitled "SURGICAL STAPLER HANDLE ASSEMBLY HAVING ACTUATION MECHANISM WITH LONGITUDINALLY ROTATABLE SHAFT" filed on Jan. 4, 2021, which is now U.S. Pat. No. 11,529,141, which is a continuation of U.S. patent application Ser. No. 16/789,152 entitled "SURGICAL STAPLER HANDLE ASSEMBLY HAVING ACTUATION MECHANISM WITH LONGITUDINALLY ROTATABLE SHAFT" filed on Feb. 12, 2020, which is now U.S. Pat. No. 10,912,565, which is a continuation of U.S. patent application Ser. No. 15/598,458 entitled "SURGICAL STAPLER HANDLE ASSEMBLY HAVING ACTUATION MECHANISM WITH LONGITUDINALLY ROTATABLE SHAFT" filed on May 18, 2017, which is now U.S. Pat. No. 10,595,866, which is a continuation of U.S. patent application Ser. No. 14/213,493 entitled "SURGICAL STAPLER HANDLE ASSEMBLY HAVING ACTUATION MECHANISM WITH LONGITUDINALLY ROTATABLE SHAFT" filed on Mar. 14, 2014, which is now U.S. Pat. No. 9,668,732, which claims priority to and benefit of U.S. Provisional Patent Application Ser. No. 61/794,700, entitled "SURGICAL STAPLER HAVING ACTUATION MECHANISM WITH ROTATABLE SHAFT," filed on Mar. 15, 2013. The entireties of these prior applications are hereby incorporated herein by reference.

BACKGROUND OF THE INVENTION

Field of the Invention

The present application relates generally to surgical occlusion instruments and, more particularly, to surgical staplers.

Description of the Related Art

Surgical staplers are used to approximate or clamp tissue and to staple the clamped tissue together. As such, surgical staplers have mechanisms to ensure that tissue is properly positioned and captured and to drive staples through the tissue. As a result, this has produced, for example, multiple triggers and handles in conjunction with complex mechanisms to provide proper stapling of the clamped tissue. With these complex mechanisms, surgical staplers can have increased manufacturing burdens, as well as potential sources for device failure and confusion for the user. Thus, reliable stapling of clamped tissue without complex mechanisms is desired.

SUMMARY OF THE INVENTION

In certain embodiments, a surgical stapler is provided herein. The surgical stapler comprises an elongate shaft, a jaw assembly, and a handle assembly. The elongate shaft has a proximal end and a distal end. The elongate shaft defines a longitudinal axis between the proximal end and the distal end. The jaw assembly is positioned at the distal end of the elongate shaft. The jaw assembly comprises a first jaw, a second jaw, and a plurality of staples. The jaw assembly is selectively positionable in one of a closed configuration, an open configuration, and a firing configuration. The handle assembly is positioned at the proximal end of the elongate shaft. The handle assembly comprises a stationary handle, a movable trigger pivotably coupled to the stationary handle, and an actuation shaft. The actuation shaft is longitudinally slidable within the handle assembly with respect to the longitudinal axis of the actuation shaft and rotatable within the handle assembly with respect to the longitudinal axis. The actuation shaft is operably coupled to the jaw assembly and the actuation shaft is longitudinally slidable in a first direction from a first position corresponding to the open configuration of the jaw assembly to a second position corresponding to the closed configuration of the jaw assembly and from the second position to a third position corresponding to the firing configuration. The actuation shaft is operably coupled to the movable trigger. The actuation shaft is rotatable between a first orientation in which movement of the trigger moves the actuation shaft between the second position and the third position and a second orientation in which movement of the trigger moves the actuation shaft from the third position to the first position.

In certain embodiments, a handle assembly for a surgical stapler is provided. The surgical stapler comprises an elongate shaft having a proximal end and a distal end, the elongate shaft defining a longitudinal axis between the proximal end and the distal end, and a jaw assembly disposed at the distal end of the elongate shaft. The handle assembly comprises a housing, a stationary handle disposed on the housing, a movable handle, an actuation mechanism, and a coupler. The movable handle is pivotably coupled to the housing and pivotable between an open position spaced apart from the stationary handle and a closed position adjacent the stationary handle. The actuation mechanism comprises an advancing driver, a reversing driver, and an actuation shaft. The advancing driver is operably coupled to the movable handle and translatable distally with respect to the longitudinal axis responsive to movement of the movable handle from the open position to the closed position. The reversing driver is operably coupled to the movable handle and translatable proximally with respect to the longitudinal axis responsive to movement of the movable handle from the open position to the closed position. The actuation shaft extends along the longitudinal axis. The actuation shaft is rotatably coupled to the housing with respect to the longitudinal axis. The actuation shaft comprises an advancing surface and a reversing surface. The advancing surface extends longitudinally along the actuation shaft. The reversing surface extends longitudinally along the actuation shaft. The reversing surface is angularly offset from the advancing surface. The actuation shaft is rotatable between a first orientation in which the advancing driver engages the advancing surface and a second orientation in which the reversing driver engages the reversing surface. The coupler is adapted to engage the elongate shaft of the surgical stapler.

In certain embodiments, a handle assembly for a surgical stapler is provided. The handle assembly comprises a housing, a trigger pivotably coupled to the housing, and an actuation mechanism. The actuation mechanism comprises a forward driver, a reverse driver, an actuation shaft, and a selector. The forward driver is operably coupled to the trigger. The reverse driver is operably coupled to the trigger.

The actuation shaft has a longitudinal axis. The actuation shaft is rotatably coupled to the housing relative to the longitudinal axis. The actuation shaft comprises a forward interface surface and a reverse interface surface angularly offset from the forward interface surface. The actuation shaft is rotatable between a first orientation in which the forward interface surface engages the forward driver to move the actuation shaft in a first direction responsive to pivotal movement of the trigger and a second orientation in which the reverse interface surface engages the reverse driver to move the actuation shaft in a second direction opposite the first direction responsive to pivotal movement of the trigger. The selector is operably coupled to the actuation shaft to selectively rotate the actuation shaft between the first orientation and the second orientation.

DETAILED DESCRIPTION OF THE INVENTION

Figure 1:
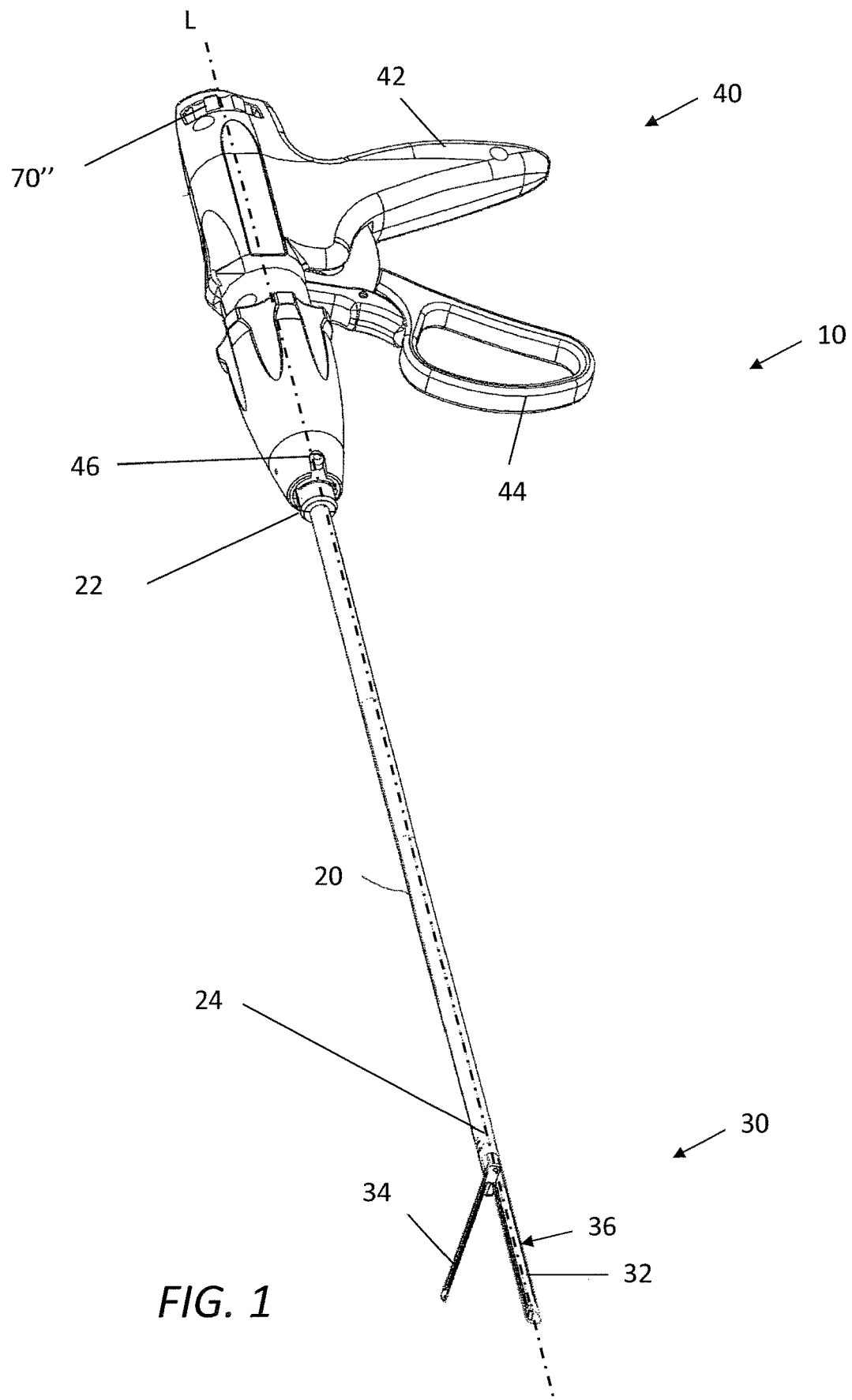
FIG. 1 is a perspective view of an embodiment of surgical stapling device with the jaws in an open configuration.
Figure 2:
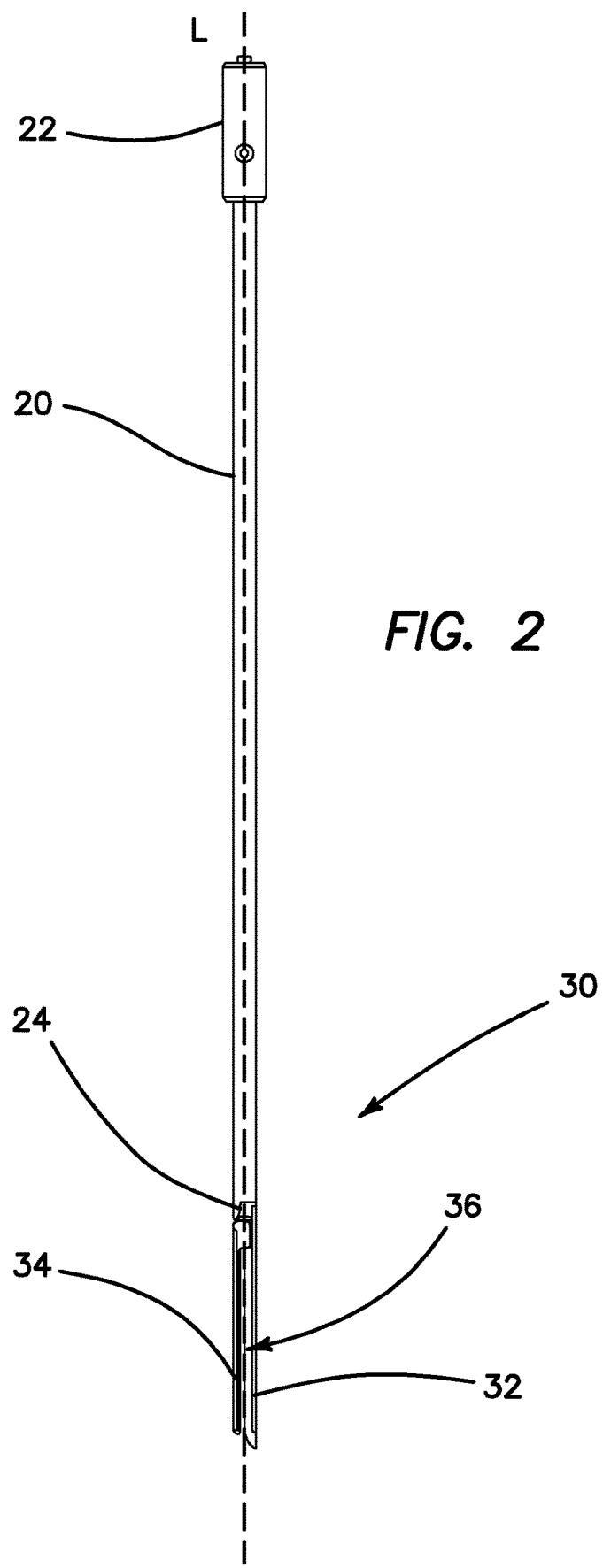
FIG. 2 is a perspective view of an embodiment of a cartridge for the surgical stapling device of FIG. 1 with the jaws in a closed configuration.

With reference to FIGS. 1-2, an embodiment of surgical stapling device is illustrated. The illustrated embodiment of surgical stapler 10 comprises an elongate shaft 20, a jaw assembly 30, and a handle assembly 40. FIG. 1 illustrates the surgical stapler 10 with the jaw assembly 30 in an open configuration. FIG. 2 illustrates a removable cartridge comprising the elongate shaft 20 and jaw assembly 30 of the surgical stapler 10 with the jaw assembly 30 in a closed configuration.

With continued reference to FIGS. 1 and 2, the illustrated embodiment of surgical stapler 10 can be sized and configured for use in laparoscopic surgical procedures. For example, the elongate shaft 20 and jaw assembly 30 can be sized and configured to be introduced into a surgical field through an access port or trocar cannula. In some embodiments, the elongate shaft 20 and jaw assembly 30 can be sized and configured to be inserted through a trocar cannula having a relatively small working channel diameter, such as, for example, less than 8 mm. In other embodiments, elongate shaft 20 and jaw assembly 30 can be sized and configured to be inserted through a trocar cannula having a larger working channel diameter, such as, for example, 10 mm, 11 mm, 12 mm, or 15 mm. In other embodiments, it is contemplated that certain aspects of the surgical staplers described herein can be incorporated into a surgical stapling device for use in open surgical procedures.

With continued reference to FIGS. 1 and 2, as illustrated, the elongate shaft 20 comprises a generally tubular member. The elongate shaft 20 extends from a proximal end 22 to a distal end 24. Elongate shaft 20 defines a central longitudinal axis, L. of the surgical stapler 10 extending between the proximal end 22 and the distal end 24.

With continued reference to FIGS. 1 and 2, in the illustrated embodiment, the jaw assembly 30 is coupled to the elongate shaft 20 at the distal end 24 of the elongate shaft 20. The jaw assembly 30 comprises a first jaw 32 and a second jaw 34 pivotally coupled to the first jaw 32. In the illustrated embodiment, the first jaw 32 is fixed to the distal end 24 of elongate shaft 20 such that it extends distally along the central longitudinal axis, L and remains stationary with respect to the elongate shaft 20. In other embodiments, it is contemplated that the jaw assembly 30 is articulable with respect to the elongate shaft 20. In an initial configuration, the first jaw 32 includes a plurality of staples 36 disposed therein.

With continued reference to FIGS. 1 and 2, in the illustrated embodiment, the jaw assembly 30 can be actuated from an open configuration (FIG. 1) to a closed configuration (FIG. 2) to a stapling configuration by an actuation member or beam that is longitudinally slidable within the elongate shaft. In an initial position, the beam can be positioned at the distal end 24 of the elongate shaft 20. With the beam in the initial position, the second jaw 34 is pivoted away from the first jaw 32 such that the jaw assembly 30 is in the open configuration. The actuation beam engages the second jaw 34 upon translation of the actuation member or beam distally along the longitudinal axis L. Translation of the actuation beam distally from the initial position a first distance can actuate the jaw assembly from the open configuration to the closed configuration. With the jaw assembly 30 in the closed configuration, the actuation beam can be returned proximally the first distance to return the jaw assembly 30 to the open configuration. A distal end of the actuation beam can advance a staple slider configured to deploy staples from the first jaw 32 such that further translation of the actuation beam distally past the first distance deploys the plurality of staples 36 from the first jaw 32.

With continued reference to FIGS. 1 and 2, in the illustrated embodiment, the handle assembly is coupled to the elongate shaft 20 at the proximal end 22 of the elongate shaft 20. As illustrated, the handle assembly 40 has a pistol grip configuration with a housing defining a stationary handle 42 and a movable handle 44 or trigger pivotably coupled to the stationary handle 42. It is contemplated that in other embodiments, surgical stapler devices including aspects described herein can have handle assemblies with other configuration such as, for example, scissors-grip configurations, or in-line configurations. As further described in greater detail below, the handle assembly 40 houses an actuation mechanism configured to selectively advance an actuation shaft responsive to movement of the movable handle 44.

In some embodiments, the surgical stapler 10 can include the plurality of staples 36 positioned in a disposable cartridge while the handle assembly 40 is configured to be reused with multiple staple cartridges. In the illustrated embodiment, the elongate shaft 20 and jaw assembly 30 define a disposable cartridge that is removably couplable to the handle assembly 40. Accordingly, in the illustrated embodiment the handle assembly 40 includes a coupler 46 at the distal end thereof. The coupler 46 is adapted to engage the elongate shaft 20 of the surgical stapler 10 The coupler 46 can have a bayonet connection having an outer connector that can removably couple the handle assembly 40 to the elongate shaft 20, and an inner connector that can removably couple the actuation shaft of the handle assembly 42 to the actuation member of the elongate shaft 20. Accordingly, the surgical stapler 10 can be configured such that the handle assembly 40 can be reused with multiple disposable cartridges during a surgical procedure. It is contemplated that in other embodiments, the handle assembly and some portion of the elongate shaft can be reusable while a remainder of the elongate shaft and the jaw assembly define a disposable cartridge. In certain other embodiments, the handle assembly and the elongate shaft can be reusable while the jaw assembly defines a disposable cartridge. In still other embodiments, a jaw insert housing a plurality of staples can define a disposable cartridge while the remainder of the surgical stapler is reasonable.

Figure 3:
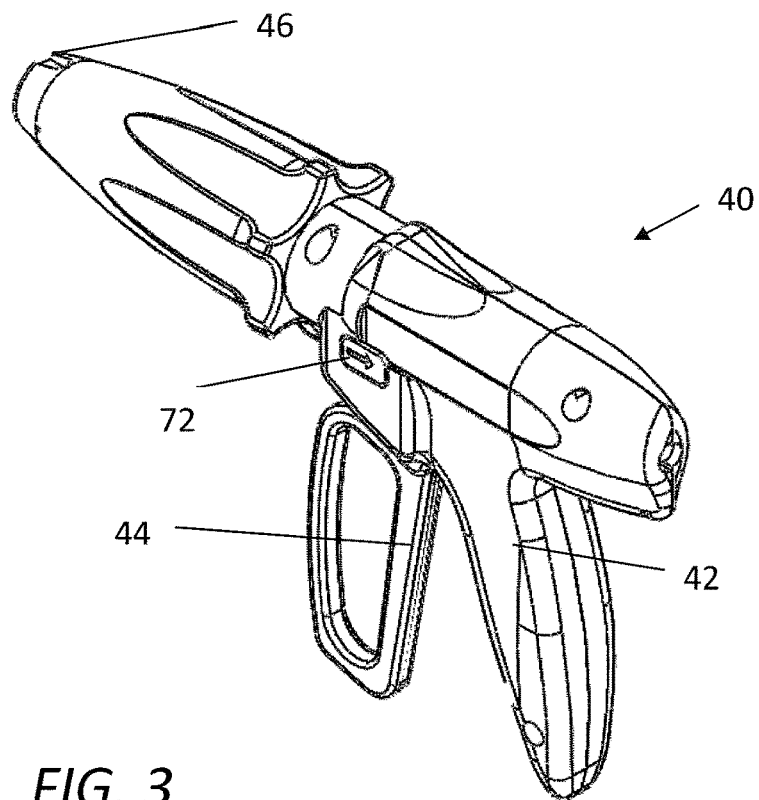
FIG. 3 is a perspective view of an embodiment of handle assembly for a surgical stapling device.

FIGS. 3-7 illustrate various views of an embodiment of handle assembly 40 for a surgical stapler 10. In FIG. 3, a perspective view of the handle assembly 40 as illustrated with the movable handle 44 in an open position spaced apart from the stationary handle 42. The illustrated handle assembly 40 further comprises a selector 72 operably coupled to the actuation mechanism housed within the handle assembly 40 as further discussed herein. As illustrated in FIG. 3, the selector 72 is in a first position.

Figure 4:
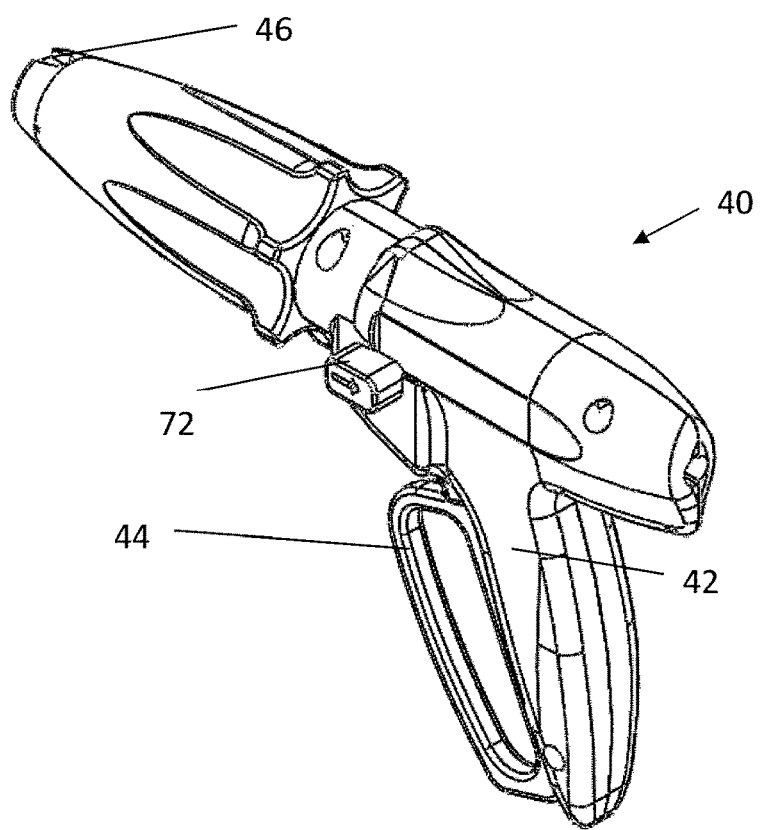
FIG. 4 is a perspective view of the handle assembly of FIG. 3 with a movable handle in a closed configuration.
Figure 5:
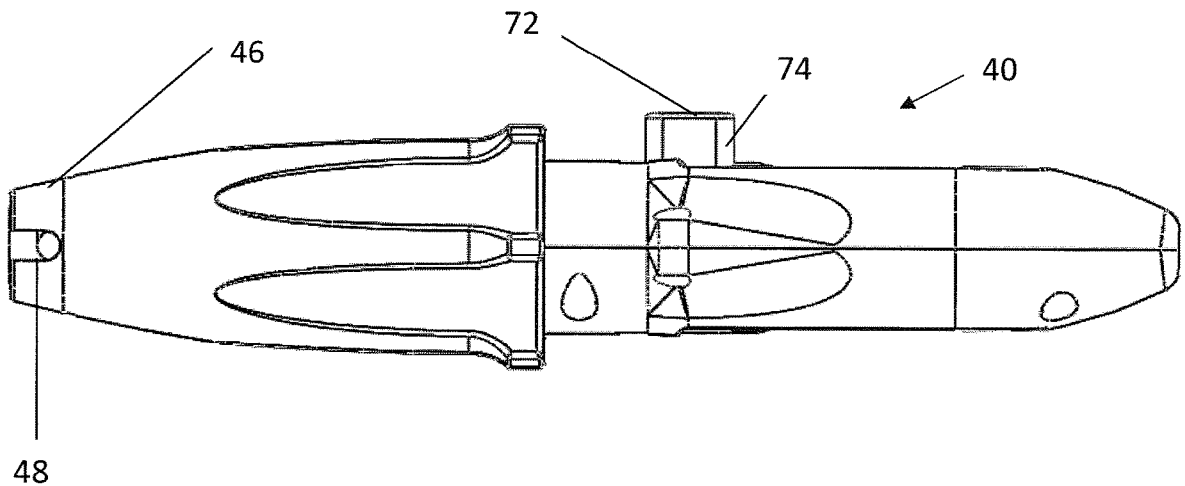
FIG. 5 is a top view of the handle assembly of FIG. 3 with a selector in a first configuration.
Figure 6:
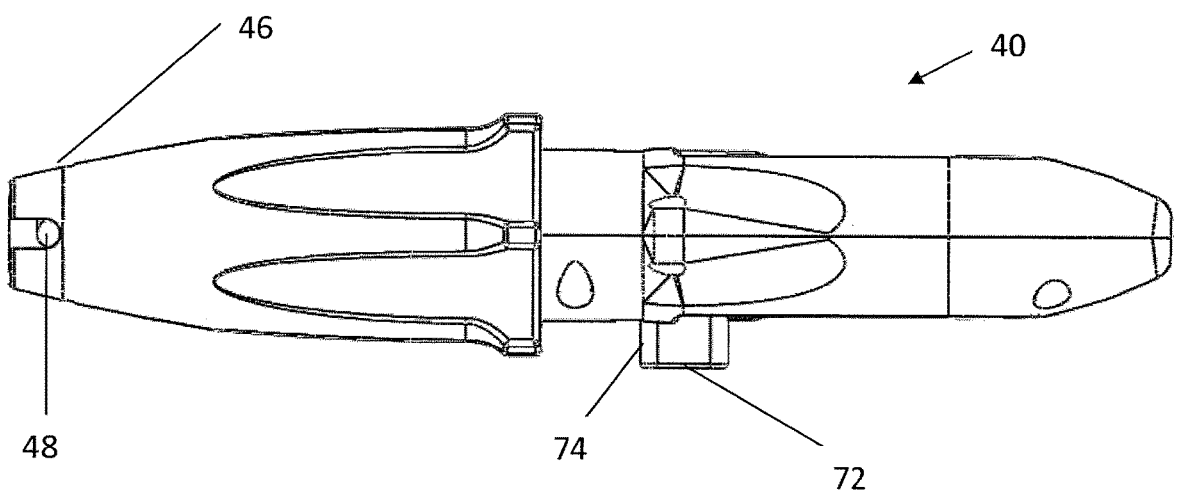
FIG. 6 is a top view of the handle assembly of FIG. 3 with a selector in a second configuration.
Figure 7:
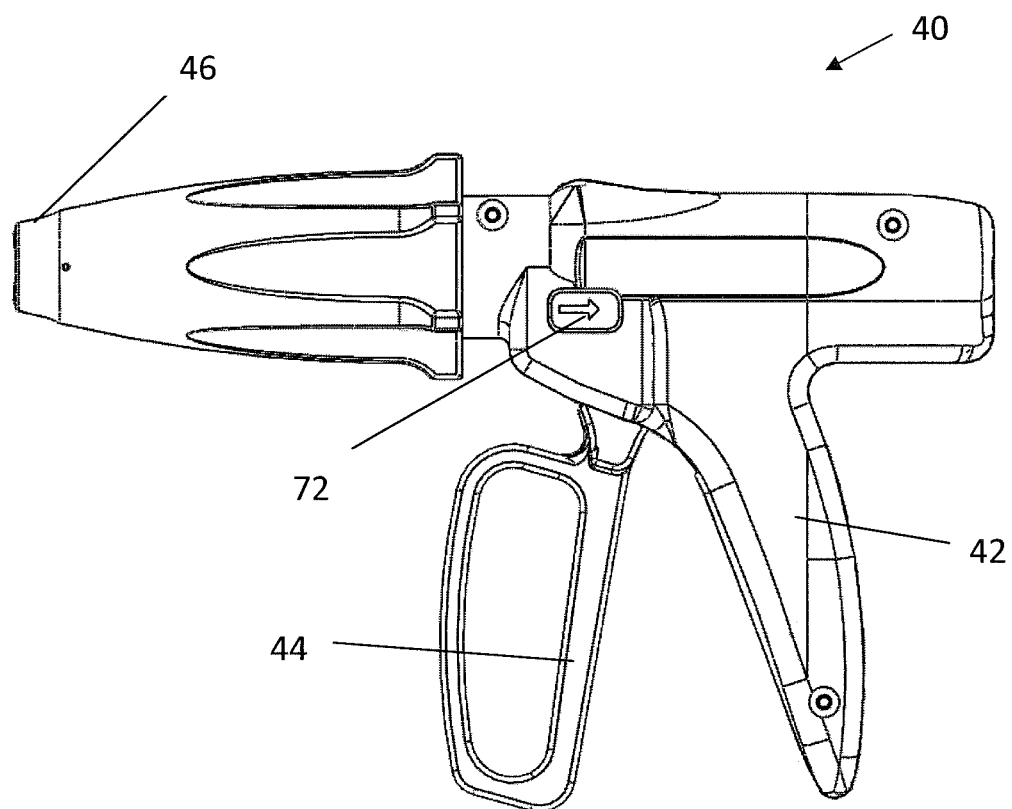
FIG. 7 is a side view of the handle assembly of FIG. 3.

With reference to FIG. 4, another perspective view of the handle assembly 40 of FIG. 3 is illustrated. As illustrated, the movable handle 44 is in a closed position positioned adjacent the stationary handle 42, and the selector 72 is in a second position. FIGS. 5 and 6 illustrate a top view of the handle assembly of FIG. 3 with the selector 72, such as a slider 74, in the first position (FIG. 5), and in the second position (FIG. 6). FIG. 7 illustrates a side view of the handle assembly 40 of FIG. 3.

Figure 8A:
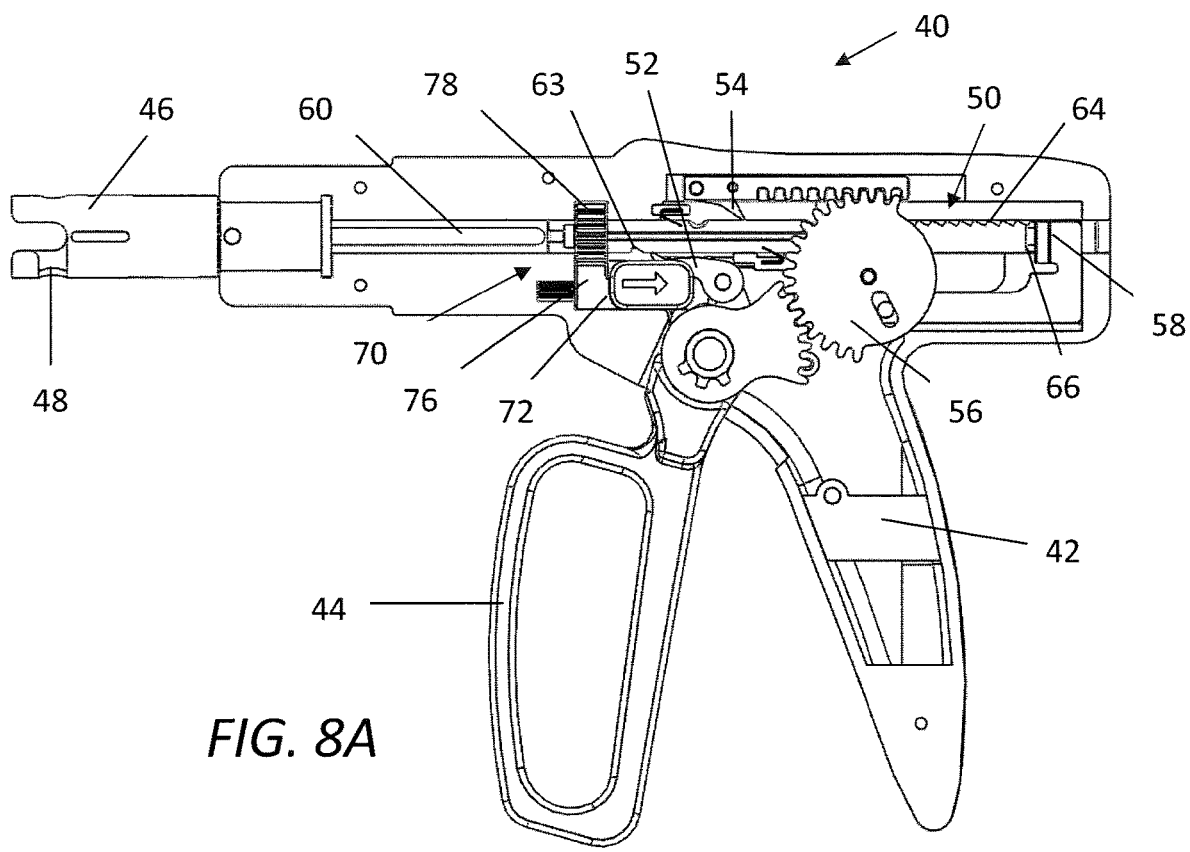
FIG. 8A is a cross-sectional side view of the handle assembly of FIG. 3 in an initial configuration.
Figure 8B:
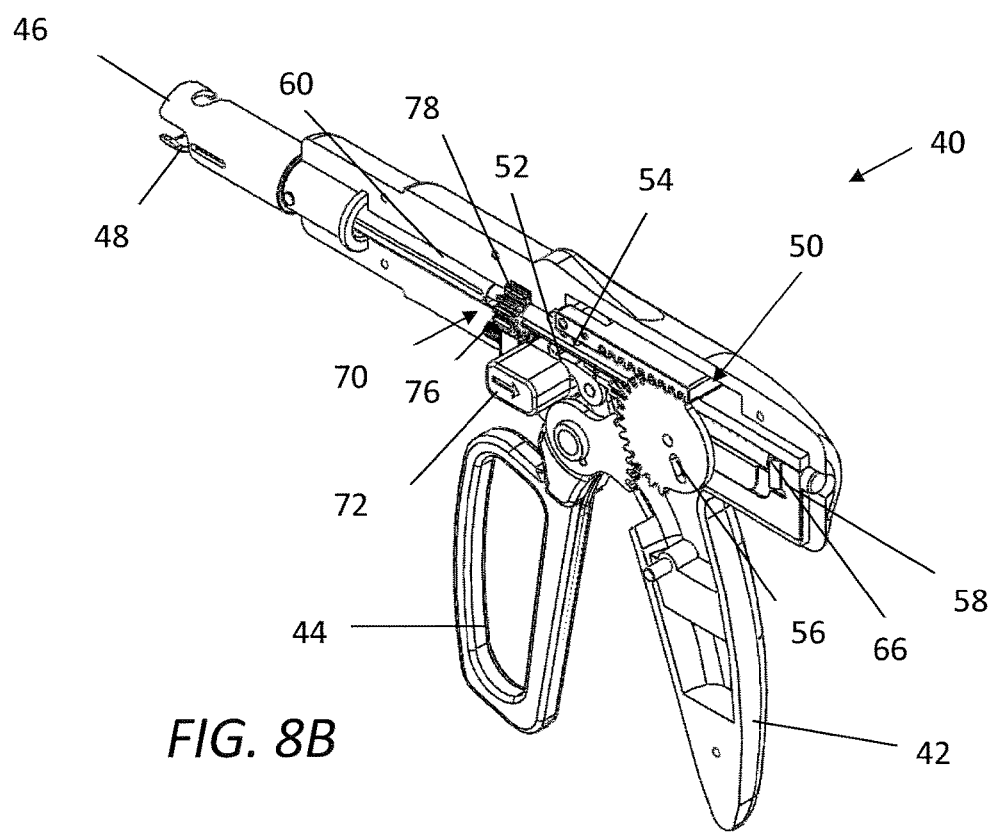
FIG. 8B is a cross-sectional perspective view of the handle assembly of FIG. 8A.

FIGS. 8A and 8B illustrate cross-sectional views of the handle assembly 40 in an initial configuration, revealing operation of the actuation mechanism 50. In the illustrated embodiment, the actuation mechanism 50 is configured to selectively translate the actuation shaft 60 from a first position corresponding to the jaw assembly 30 being in the open configuration to a second position corresponding to the jaw assembly 30 being in the closed configuration and from the second position to a third position to position the jaw assembly 30 in a stapling configuration and deploy the plurality of staples 36. In the initial configuration illustrated in FIGS. 8A and 8B, actuation mechanism 50 can repeatedly translate the actuation shaft 60 between the first position and the second position responsive to movement of the movable handle 44 or trigger without deploying the staples to provide an open and close functionality. This open and close functionality allows a user to position, clamp tissue, and reposition the stapler 10 to find a desirable staple placement location before deploying the staples.

With reference to FIGS. 8-14, in the illustrated embodiment, the actuation mechanism comprises an advancing or forward driver 52, a reverse driver 54, an opening driver 58, an advancing surface 62, a reversing surface 64, and an opening surface 66. The forward driver 52 can be operably coupled to the movable handle 44 such that movement of the movable handle 44 from the open position to the closed position advances the forward driver 52 in a first direction such as for example distally within the handle assembly 40. The forward driver 52 can comprise a pawl or tooth configured to engage a recess or slot.

The reverse driver 54 can be operably coupled to movable handle 44 such that movement of the movable handle 44 from the open position to the closed position advances the reverse driver 54 in a second direction opposite the first direction such as, for example proximally within the handle assembly 40. In some embodiments, the movable handle 44 can be operably coupled with the reverse driver 54 with a geared connection including an idler gear 56. The reverse driver 54 can comprise a pawl or tooth configured to engage a recess or slot.

The opening driver 58 can be operably coupled to the movable handle 44 such that movement of the movable handle 44 from the open position to the closed position advances the opening driver 58 in a first direction such as for example distally within the handle assembly 40. In the illustrated embodiment, the opening driver 58 is coupled to the idler 56 with a pin and slot connection to operably couple the opening driver 58 to the movable handle 44. The opening driver 58 can comprise a pawl or tooth configured to engage a recess or slot.

The actuation shaft 60 includes advancing surface 62, reversing surface 64, and opening surface 66 formed thereon. In the illustrated embodiment, the advancing surface 62 comprises a rack, or plurality of spaced recesses or teeth formed longitudinally along the actuation shaft 60. As illustrated, reversing surface 64 comprises a rack or plurality of space recesses or teeth formed longitudinally along the actuation shaft 60 and angularly offset from the advancing surface 62. In the illustrated embodiment, the opening surface 66 comprises a recess formed in the actuation shaft 60.

In certain embodiments, the actuation shaft 60 is rotatable within the handle assembly 40 about the longitudinal axis of the stapler 10. The handle assembly 40 can comprise a rotation mechanism 70 to provide selective rotation of the actuation shaft 60 within the handle assembly 40. The actuation shaft 60 can be rotatable between a first orientation in which the forward driver 52 is engageable with the advancing surface 62 and a second orientation in which the reverse driver 54 is engageable with the reversing surface 64. With the angular offset of the advancing surface 52 from the reversing surface 54 with respect to the actuation shaft 60, with the actuation shaft in the first orientation, the reverse driver 54 is disengaged from the reversing surface 64, and with the actuation shaft in the second orientation, the forward driver 52 is disengaged from the advancing surface 62.

With continued reference to FIGS. 8-14, in certain embodiments, the rotation mechanism 70 comprises a selector 72, such as a slider. The slider can extend transversely through the housing of the handle assembly 40. The slider can be operably coupled to the actuation shaft 60 such that positioning the slider in the first position extending from one side of the handle assembly 40 positions the actuation shaft 60 in the first orientation, and positioning the slider in the second position extending from an opposite side of the handle assembly 40 rotates the actuation shaft 60 to the second orientation. In the illustrated embodiment, the slider is coupled to a rack 76 in meshing engagement with a gear 78 that is rotatably fixed to the actuation shaft 60 and longitudinally slidable along the actuation shaft 60 (such as, for example, with a keyed connection). Desirably, the illustrated rotation mechanism 70 including a slider discretely positions the actuation shaft 60 in a desired orientation, reducing the incidence of the mismeshed gearing within the actuation mechanism 50. In some embodiments the slider can include visual indicators, such as arrows, to indicate the orientation of the actuation shaft 60, and thus, the actuation mode of the stapler to a user.

In the illustrated embodiment, the advancing surface 62 and the reverse surface 64 are angularly offset by approximately 90 degrees about the actuation shaft. Thus, the rotation mechanism 70 is configured to rotate the actuation shaft approximately 90 degrees between the first orientation and the second orientation. In other embodiments, the actuation surface 62 and the reverse surface 64 can have a different angular offset, such as, for example 120 degrees, and the rotation mechanism 70 can be configured to rotate the actuation shaft 60 correspondingly. Moreover, as described in further detail herein with respect to an open/close mode of the handle assembly 40 operation, in the illustrated embodiment, the opening driver 58 engages with the actuation shaft in the second orientation, in other embodiments, the actuation shaft can be rotatable to a third orientation in which the opening driver 58 engages with the actuation shaft.

With reference to FIGS. 8-14, a typical operation sequence of the actuation mechanism 50 of the handle assembly 40 is illustrated. FIGS. 8A-8B and 9A-9B illustrate operation of the handle assembly 40 in an initial configuration providing an open/close functionality to the jaw assembly 30. In FIG. 8A, the movable trigger 44 is at an open position, and the actuation shaft 60 is at a first position, corresponding to the first position of the actuation beam at the distal end of the elongate shaft 20. In the initial position, the actuation shaft 60 is positioned at the second orientation such that the reverse driver 54 is angularly aligned with the reversing surface 64. With actuation shaft 60 in the second orientation, the opening driver 58 is positioned within the opening surface 66 or recess. Movement of the movable handle 44 from the open position (FIG. 8A-8B) to the closed position (FIG. 9A-9B), advances the forward driver 52 distally along the actuation shaft 60 to engage an advancing recess 63 formed in the actuation shaft 60 and drive the actuation shaft 60 distally in the handle assembly 40 to a second position. The second position of the actuation shaft 60 within the handle assembly 40 corresponds to the second position of the actuation beam, which positions the jaw assembly 30 in a closed configuration.

Figure 11A:
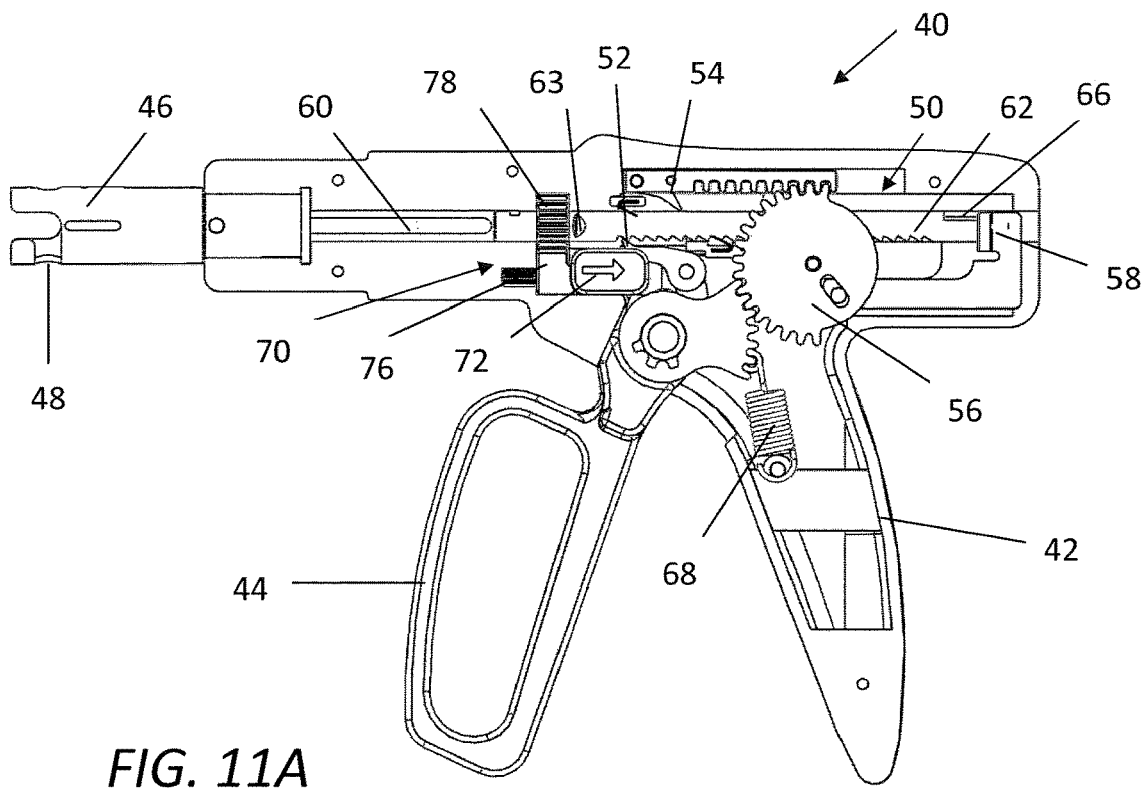
FIG. 11A is a cross-sectional side view of the handle assembly of FIG. 3 in the forward drive configuration.
Figure 11B:
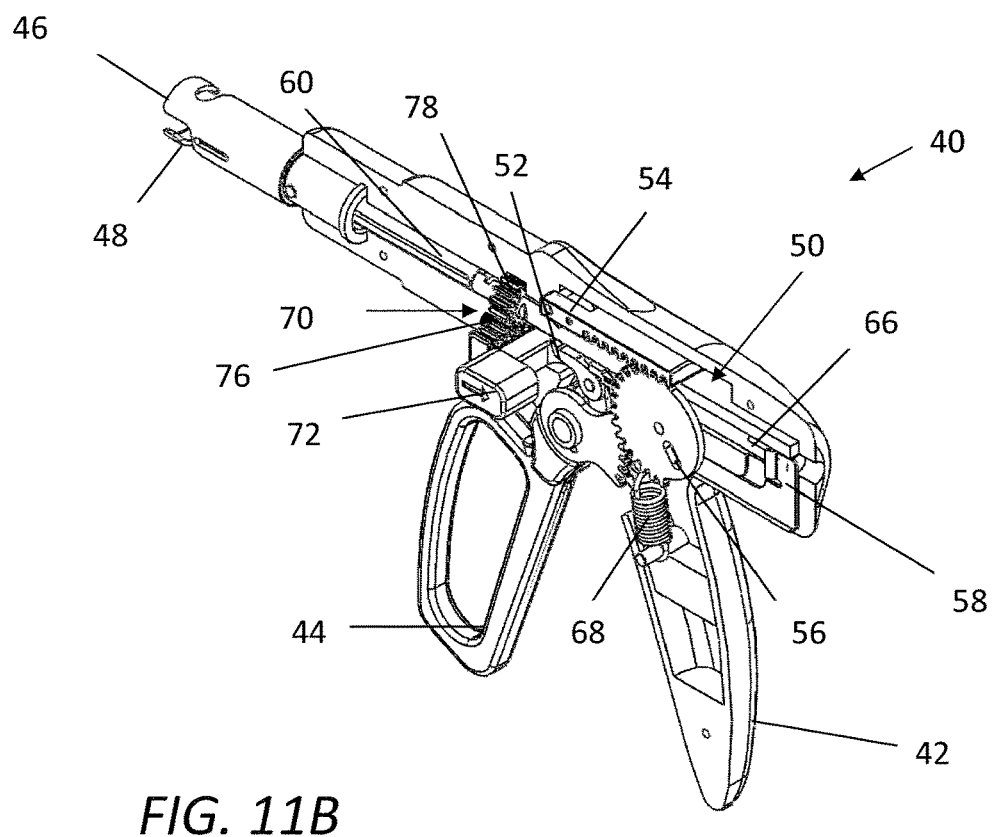
FIG. 11B is a cross-sectional perspective view of the handle assembly of FIG. 11A.

The movable handle 44 can be biased to the open position by a biasing member, such as a coil spring 68 (FIG. 11A). Thus, releasing the movable handle 44 from the closed position illustrated in FIG. 9A-9B would return it to the open position of FIGS. 8A-8B. Operable coupling of the movable handle 44 to the opening driver 58 would likewise translate the opening driver 58 proximally within the handle assembly 40 as the movable handle 44 returns to the open position. In the second orientation of the actuation shaft 60, the opening driver 58 engages opening surface 66 such that the proximal movement of the opening driver 58 returns the actuation shaft 60 from the second position to the first position, returning the jaw assembly 30 to the open configuration.

Figure 9A:
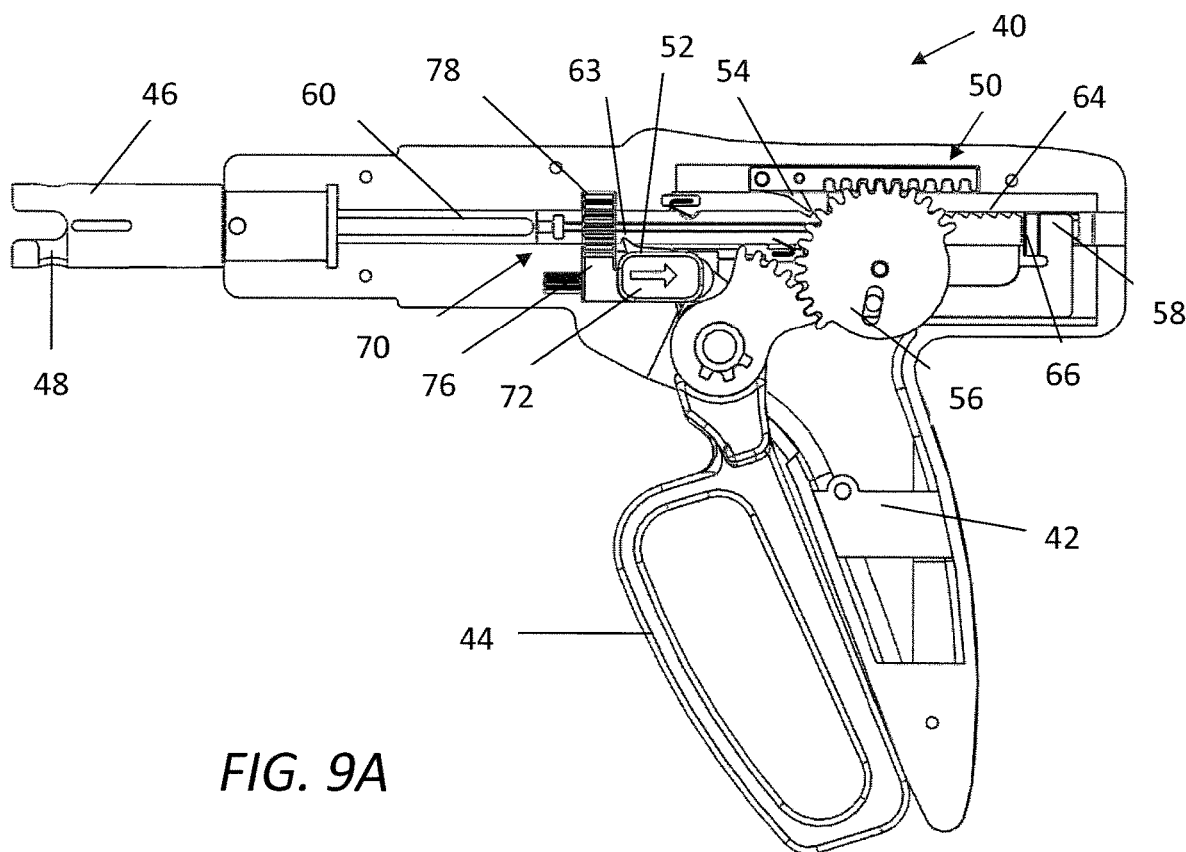
FIG. 9A is a cross-sectional side view of the handle assembly of FIG. 3 actuated to a closed configuration.
Figure 9B:
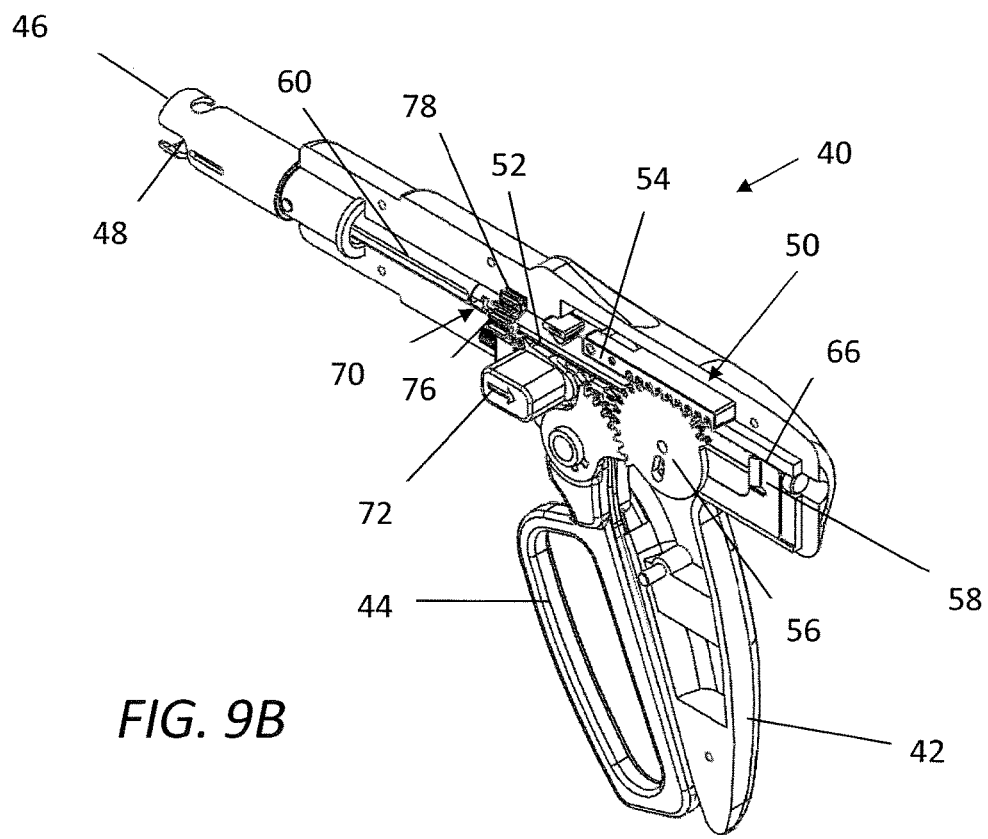
FIG. 9B is a cross-sectional perspective view of the handle assembly of FIG. 9A.
Figure 10A:
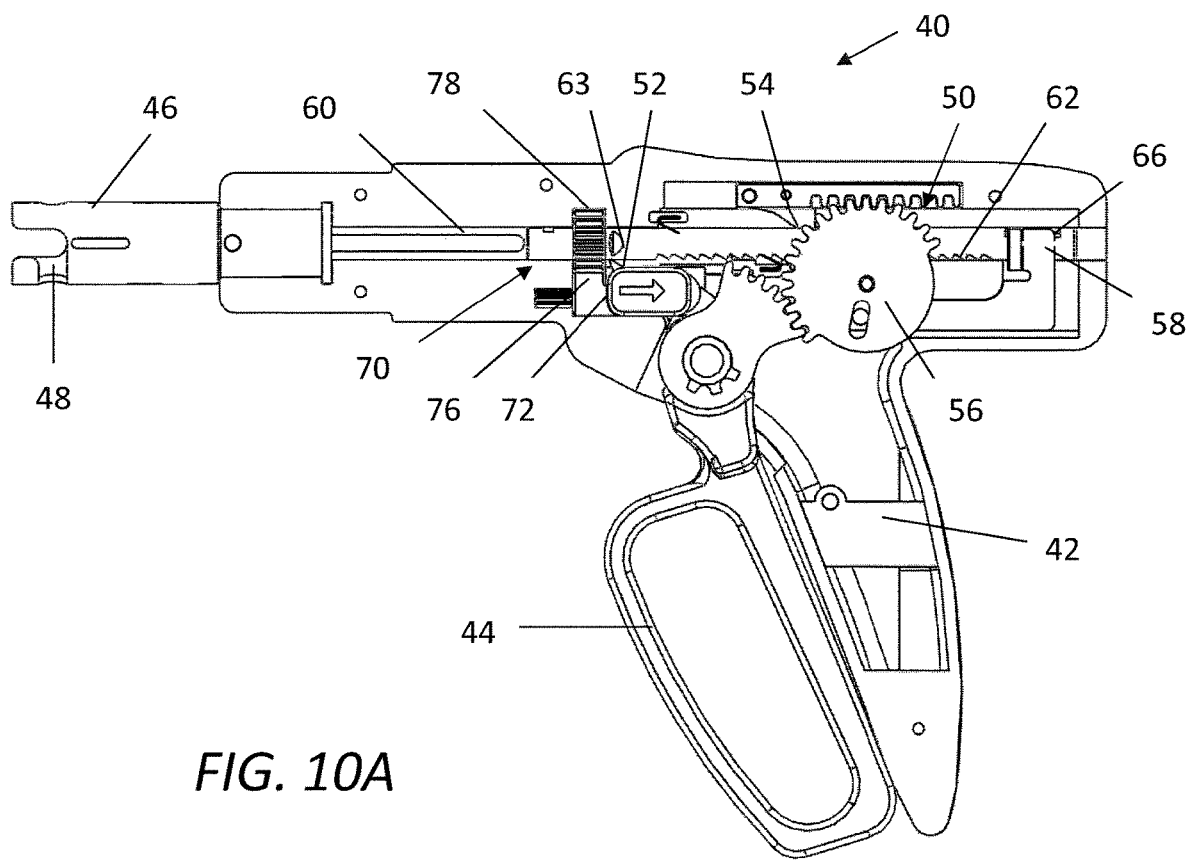
FIG. 10A is a cross-sectional side view of the handle assembly of FIG. 3 in a forward drive configuration.
Figure 10B:
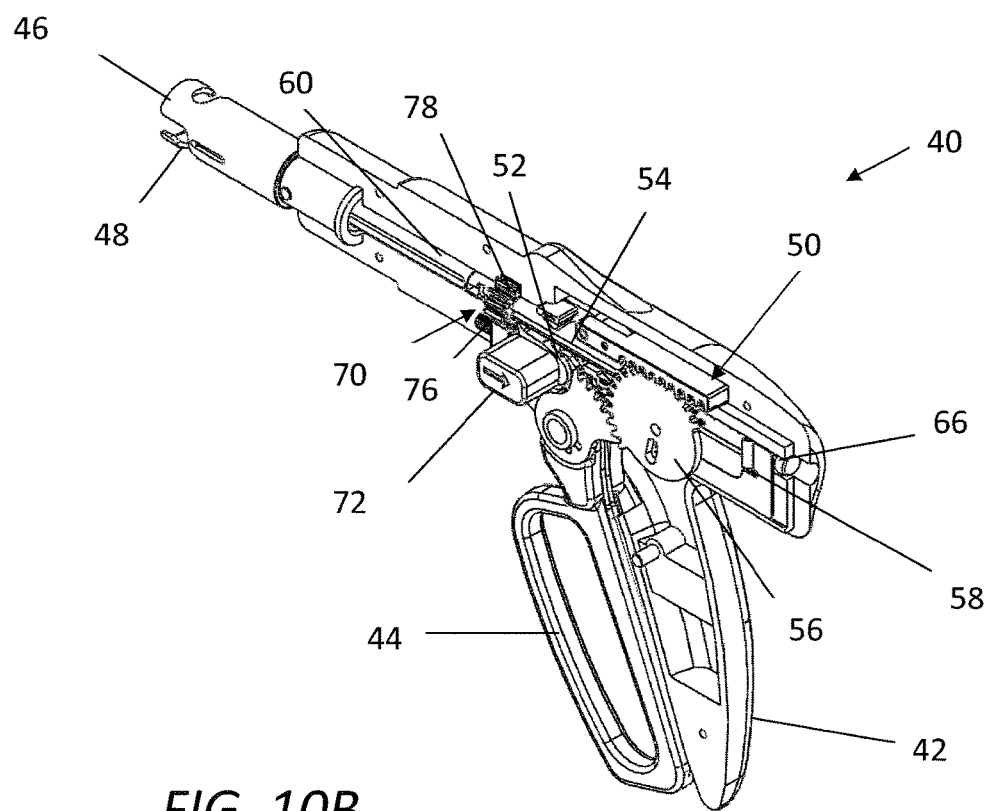
FIG. 10B is a cross-sectional perspective view of the handle assembly of FIG. 10A.

A user can seek a desired stapling position within a surgical field by repeatedly opening and closing the jaws to clamp tissue in various locations. Once a desired stapling position has been selected, the actuation mechanism 50 can be configured in a stapling or firing mode by rotating the actuation shaft 60 to the first orientation. With the jaw assembly a closed configuration at a desired stapling position (as illustrated in FIGS. 9A-9B), a user can reposition the selector 72 by sliding the slider to the first position, corresponding to the first orientation of the actuation shaft 60 (as illustrated in FIGS. 10A-10B). In the first orientation of the actuation shaft 60, the forward driver 52 is engageable with the advancing surface 62, the reversing driver 54 is angularly misaligned with the reversing surface 64, and the opening driver 58 angularly misaligned with the opening surface 66. With the actuation shaft 60 in the first orientation, the movable handle 44 can be released into the open position (FIG. 11A-11B), engaging the forward driver 52 with the advancing surface 62.

Figure 12A:
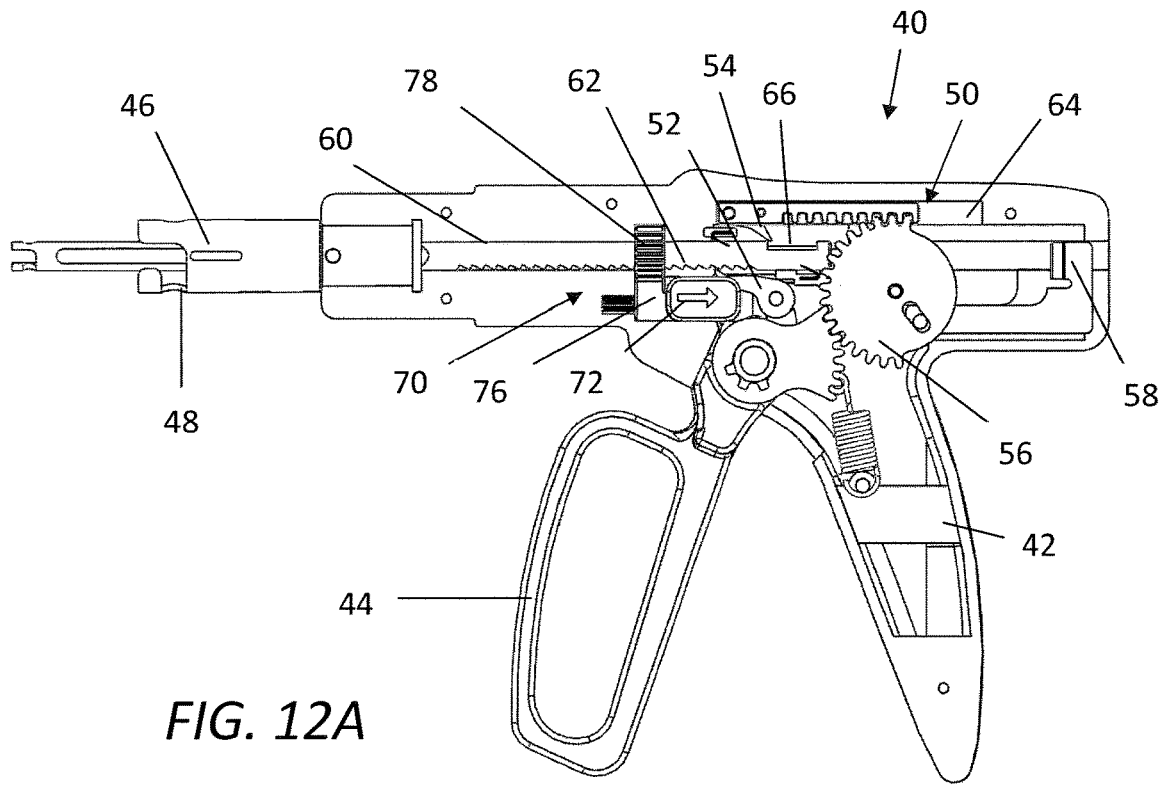
FIG. 12A is a cross-sectional side view of handle assembly of FIG. 3 in a fully driven forward configuration.
Figure 12B:
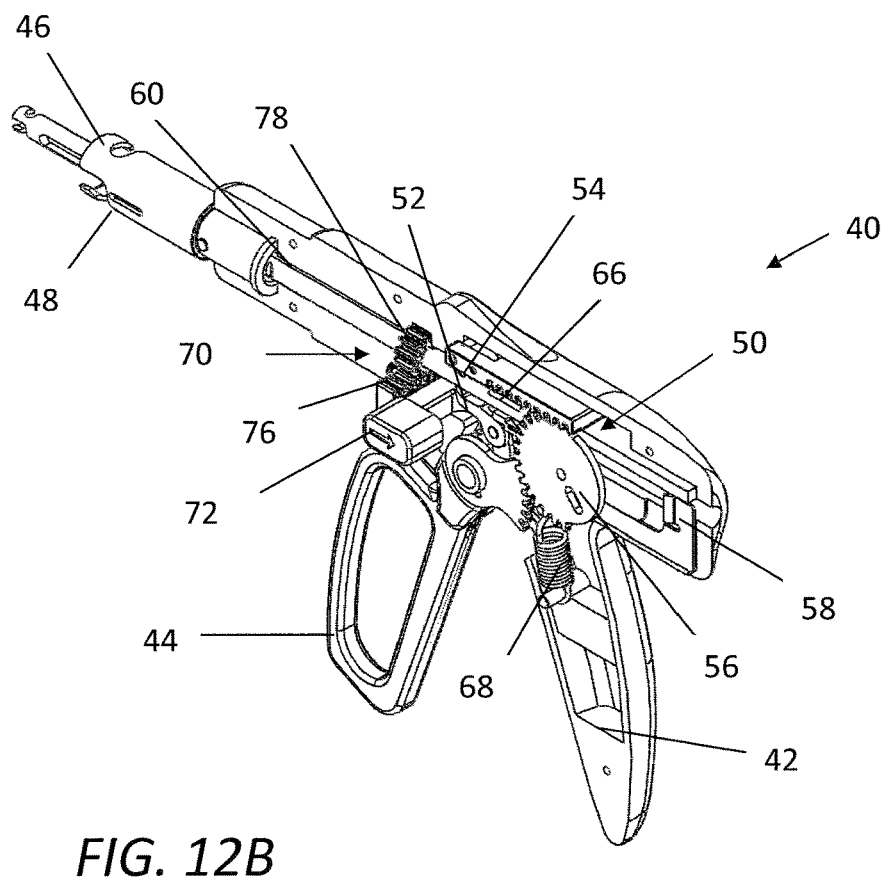
FIG. 12B is a cross-sectional perspective view of the handle assembly of FIG. 12A.

With reference to FIGS. 11A-11B and 12A-12B, with the actuation shaft 60 in the first orientation, and the forward driver 52 engaging the advancing surface 62, the actuation mechanism 50 is in a stapling or firing mode. Several cycles of movable handle 44 movement from the open position to the closed position and back to the open position advance the actuation shaft 60 from the second position (FIGS. 11A-11B), to a third position in which the actuation shaft 60 is moved to its distal-most limit with respect to the handle assembly 40 (FIGS. 12A-12B). In some embodiments, the actuation mechanism can include a stop to interfere with distal travel of the actuation shaft 60 at the third position. The second position of the actuation shaft corresponds to the second position of the actuation beam in the jaw assembly 30. The third position of the actuation shaft corresponds to the third position of the actuation beam in the jaw assembly 30 in which the plurality of staples have been deployed from the first jaw. With movement of the movable handle 44 or trigger in the firing mode to advance the actuation shaft from the second position to the third position, the forward driver 52 is sequentially advanced over the adjacent teeth or grooves of the actuating surface 62 in a ratchet-like advancement.

Figure 13A:
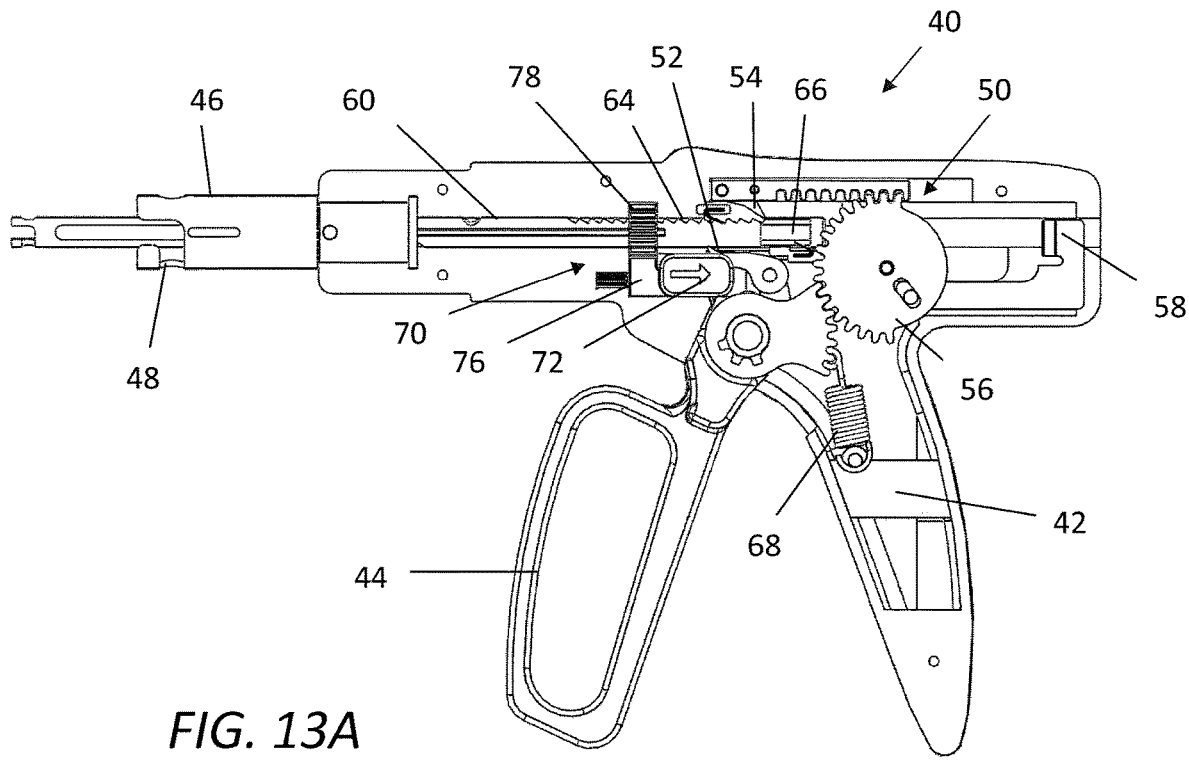
FIG. 13A is a cross-sectional side view of the handle assembly of FIG. 3 in a reverse drive configuration.
Figure 13B:
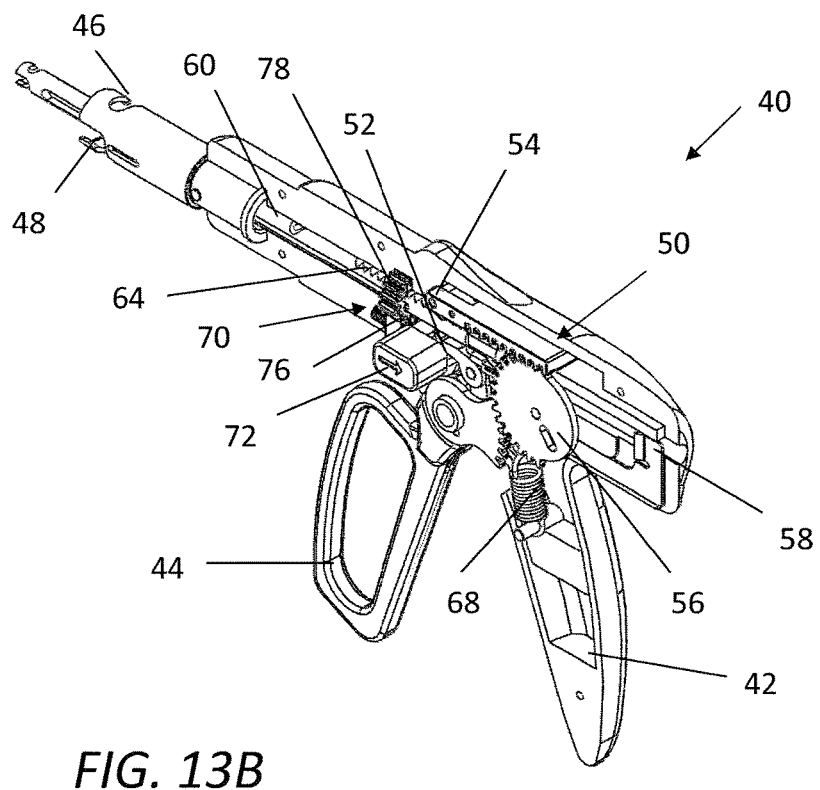
FIG. 13B is a cross-sectional perspective view of the handle assembly of FIG. 13A.
Figure 14A:
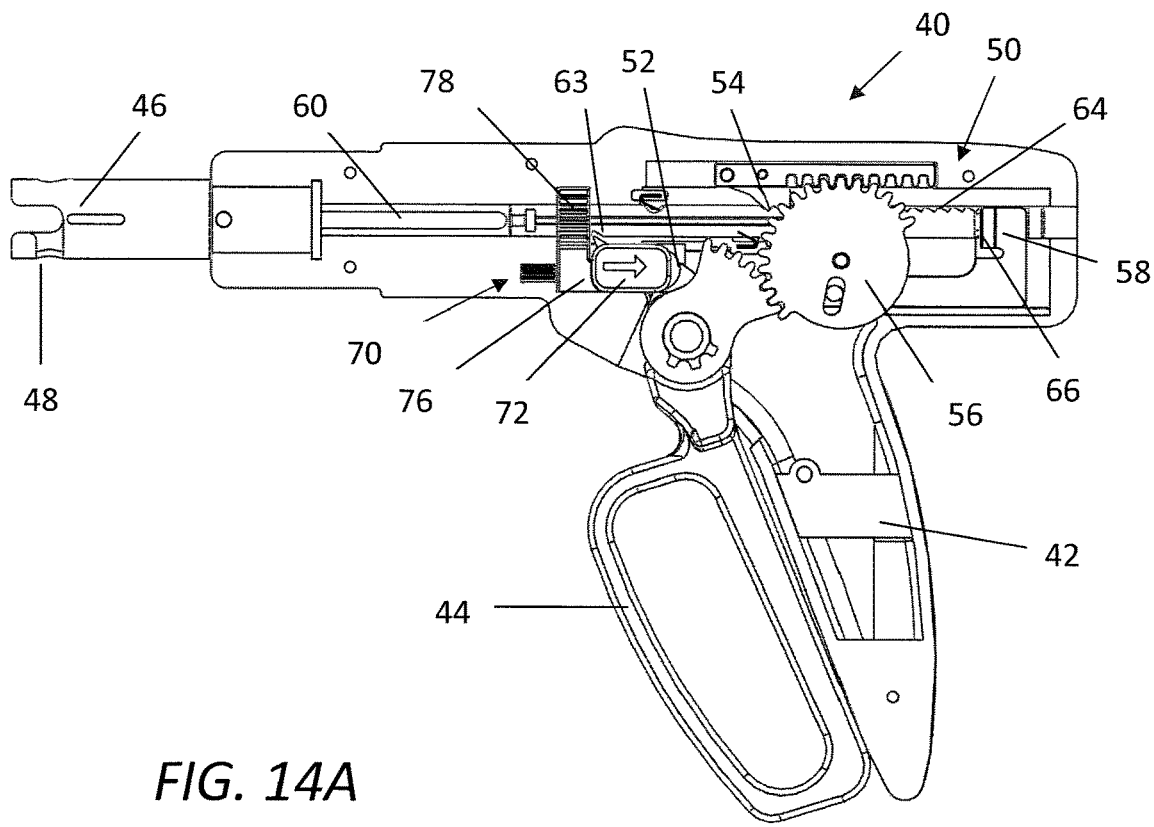
FIG. 14A is a cross-sectional side view of the handle assembly of FIG. 3 in a fully driven reverse configuration.
Figure 14B:
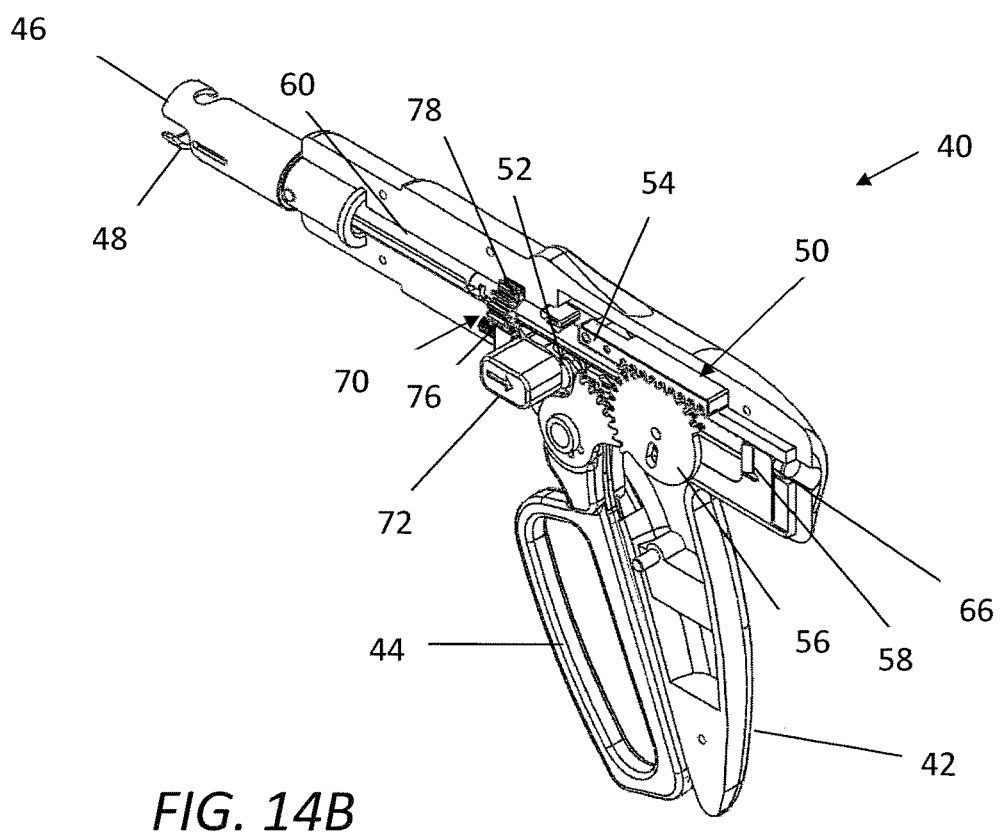
FIG. 14B is a cross-sectional perspective view of the handle assembly of FIG. 14A.

With reference to FIGS. 13A-13B, once the actuation shaft 60 has been advanced to the third position and the staples have been fired from the jaw assembly, the actuation mechanism 50 can be configured in a reverse mode. Accordingly, the rotation mechanism 70 can rotate the actuation shaft 60 to the second orientation to position the reversing surface 64 in angular alignment with the reverse driver 54. The slider can be slid to the second position to rotate the actuation shaft from the first orientation (FIGS. 12A-12B) to the second orientation (FIGS. 13A-13B). With the actuation shaft 60 in the second orientation, repeated cycles of the movable handle 44 from the open position to the closed position and back to the open position engage the reverse driver 54 with the reversing surface 64 in a ratchet-like advancement while retracting the actuation shaft 60 proximally in the handle assembly 40. Once the reverse driver 54 has driven the actuation shaft 60 proximally to the second position (illustrated in FIGS. 14A-14B), the opening driver 58 engages the opening surface 66. The opening driver 58 returns the actuation shaft 60 to the first position when the movable handle 44 is released to the open position. (Returning the handle assembly to the configuration illustrated in FIGS. 8A-8B). With the actuation shaft 60 in the first position, the cartridge, emptied of staples, can be decoupled from the handle assembly 40 and a new cartridge can be coupled to the handle assembly to begin another stapling operation.

Figure 15:
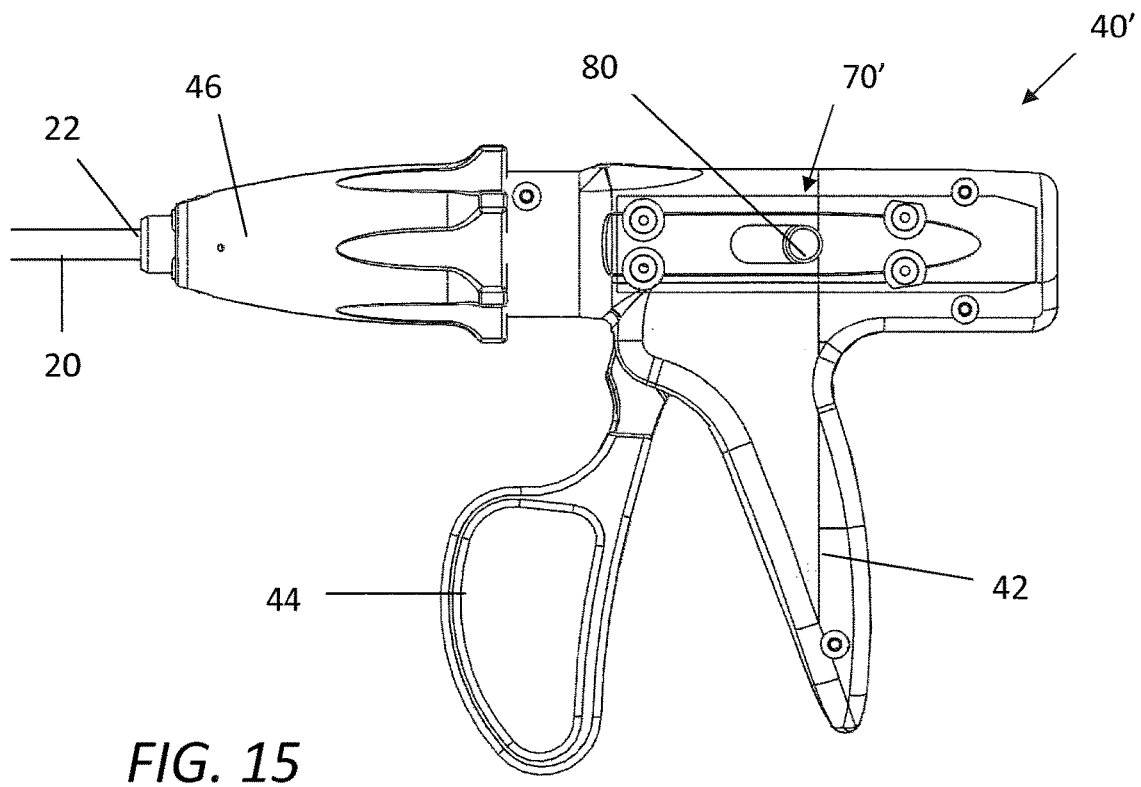
FIG. 15 is a side view of another embodiment of handle assembly for a surgical stapling device.
Figure 16:
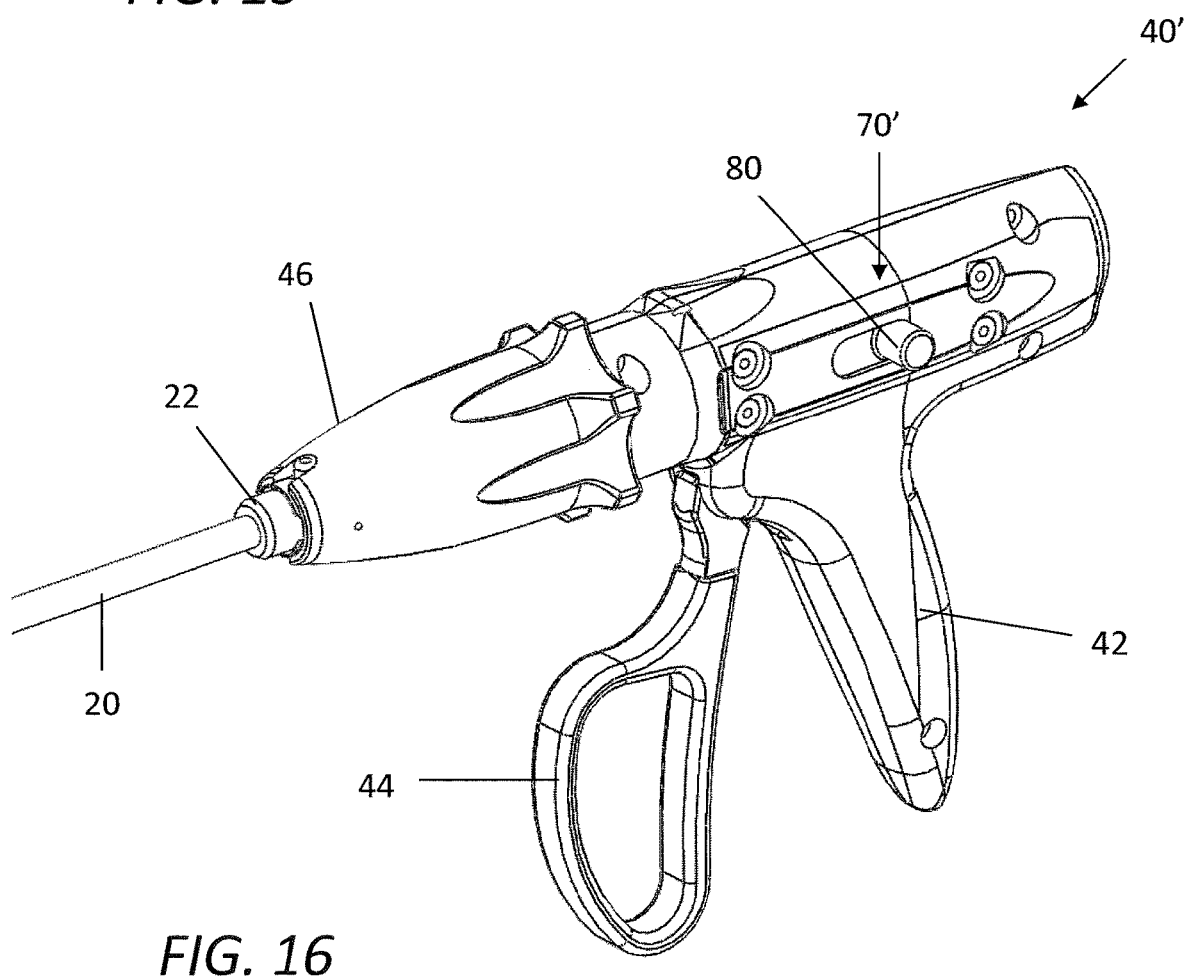
FIG. 16 is a perspective view of the handle assembly of FIG. 15.

With reference to FIGS. 15-25, another embodiment of handle assembly 40' for use with a surgical stapler 10' is illustrated. FIG. 15 illustrates a side view of the handle assembly 40', and FIG. 16 illustrates a perspective view of the handle assembly 40'. In the handle assembly 40', actuation of the rotation mechanism 70' is accomplished with a slidable switch 80 that is longitudinally slidable with respect to the handle assembly 40' housing. Advantageously, such a slidable switch arrangement can allow a user to easily rotate the actuation shaft 60 in a single-handed operation.

Figure 17:
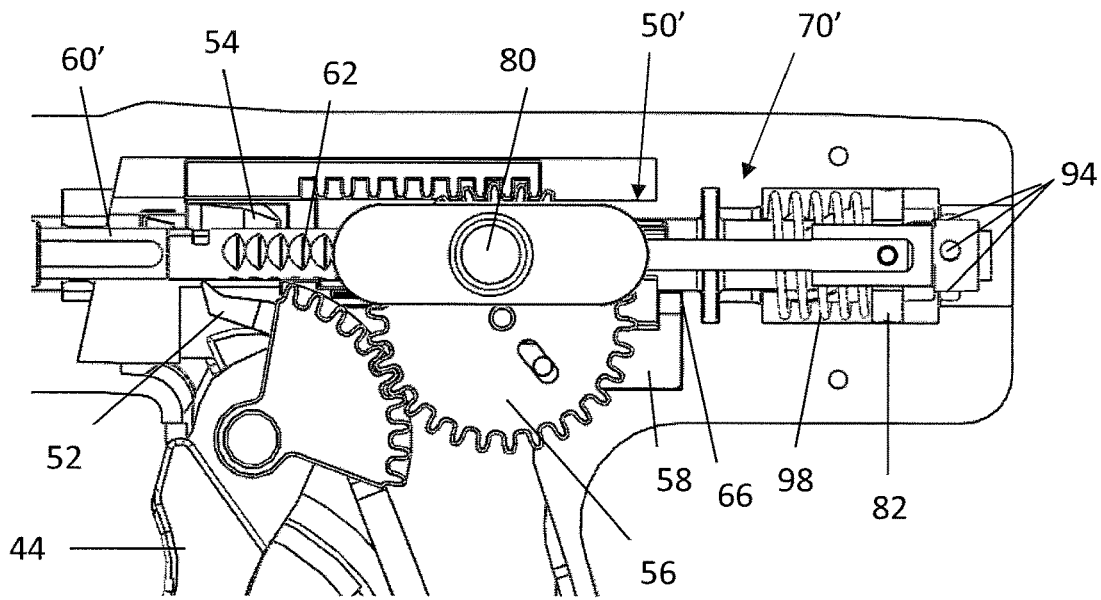
FIG. 17 is a cutaway side view of the handle assembly of FIG. 15.

With reference to FIG. 17, a cross-sectional view of the handle assembly 40' is illustrated revealing the actuation mechanism 50' and the rotation mechanism 70'. The actuation mechanism functions substantially as described above with respect to the embodiment of FIGS. 8A, 8B-14A, 14B to advance the actuation shaft 60' from a first position to a second position in an open/close mode, from the second position to a third position in a stapling mode, and from the third position to the first position in a reverse mode. The actuation mechanism 50' includes corresponding forward, reverse, and opening drivers 52, 54, 58 operably coupled to a movable handle 44 and advancing 62, reversing, and opening surfaces on the actuation shaft 60' substantially as described with respect to the embodiment of FIGS. 8A, 8B-14A-14B. However, in the embodiment illustrated in FIGS. 15-25, the actuation shaft 60' is rotatable by the rotation mechanism 70' discretely between a first orientation corresponding to the open/close mode of the handle assembly wherein the opening driver 58 engages the opening surface 66, a second orientation corresponding to the stapling position, wherein the forward driver 52 engages the advancing surface 62, and a third orientation corresponding to the reverse position wherein the reverse driver 54 engages the reversing surface.

Figure 18:
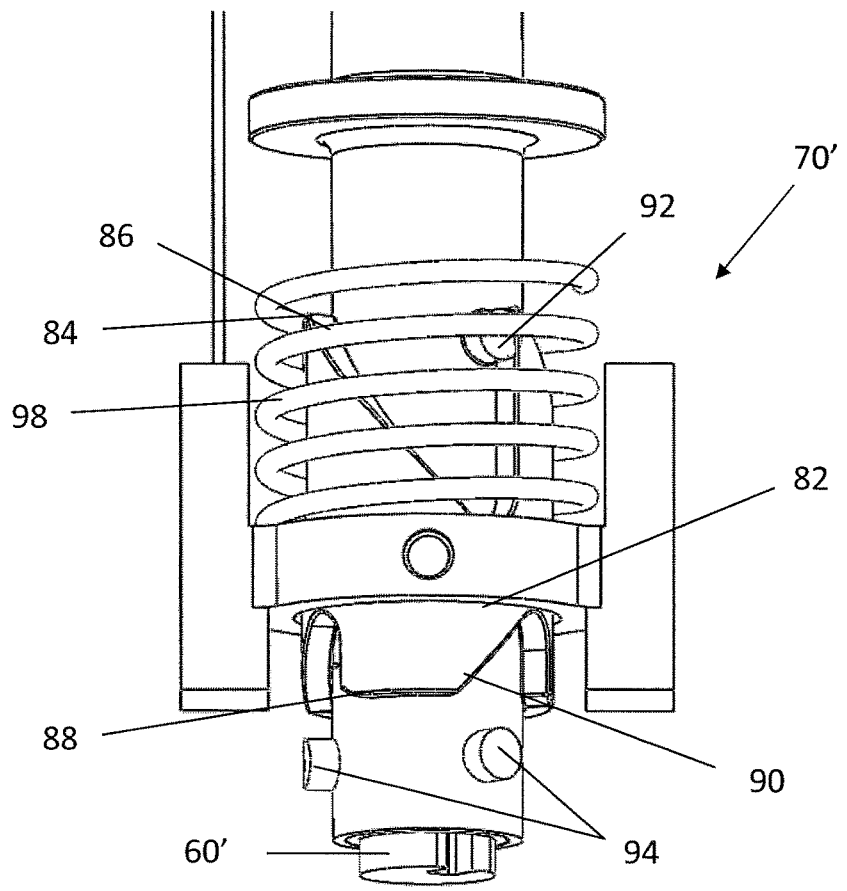
FIG. 18 is a top view of a rotation mechanism for an actuation mechanism of the handle assembly of FIG. 15.

With reference to FIGS. 17-18, certain aspects of the rotation mechanism 70' are illustrated. The rotation mechanism 70' comprises the slidable switch 80 longitudinally slidable with respect to the housing of the handle assembly 40', a hub collar 82 longitudinally slidable by the switch 80, and a biasing member or spring 98. In the illustrated embodiment, the slidable switch 80 is connected to the hub collar 82 with a thin beam, such as a shim member. The hub collar 82 is rotationally fixed and longitudinally slidable with respect to the housing of the handle assembly 40'. In some embodiments, the hub collar 82 can comprise first and second wings that can slide in corresponding first and second slots in the housing of the handle assembly to allow relative longitudinal movement and restrict relative rotational movement therebetween.

The hub collar 82 can be a generally tubular member disposed around the actuation shaft 60'. The hub collar 82 can extend between a first edge 84 having a plurality of ramps 86 formed therein and a second edge 88 having a plurality of recesses 90 formed therein. In the illustrated embodiment, the hub collar 82 comprises three ramps 86 formed in the first edge 84 with each ramp spaced approximately 120 degrees apart from adjacent ramps 86. As illustrated, the hub collar 82 comprises three recesses 90 formed in the second edge 88 with each recess 90 being approximately 120 degrees apart from adjacent recesses 86. In other embodiments, the number and relative spacing of ramps 86 and recesses 90 can vary to rotate the actuation shaft 50 between different orientations from those of the illustrated embodiment.

In some embodiments, the rotation mechanism 70' can include a spring 98 to bias the slidable switch 80 and the hub collar 82 to a proximal position with respect to the housing of the handle assembly 40'.

With continued reference to FIGS. 17-18, the actuation shaft 60' can have a first plurality of projections 92 projecting radially outwardly therefrom adjacent the first edge 84 of the hub collar 82. In the illustrated embodiment, the actuation shaft has three projections 92 each spaced approximately 120 degrees from the adjacent projections. The actuation shaft 60' can further comprise a second plurality of projections 94 extending radially outwardly from the actuation shaft 60' at a position adjacent the second edge 88 of the hub collar 82. In the illustrated embodiment, the actuation shaft 60' has three projections 94 each spaced approximately 120 degrees from the adjacent projections. In other embodiments, the numbers and spacing of the projections 92, 94 can be varied to achieve a rotation mechanism with different rotational characteristics. In some embodiments, the projections 92, 94 can be formed on the actuation shaft 60', while in other embodiments, the projections 92, 94 can be formed separately such as on a sleeve that is adhered to, has a keyed engagement with, or is otherwise rotationally fixed to the actuation shaft 60'.

Figure 19:
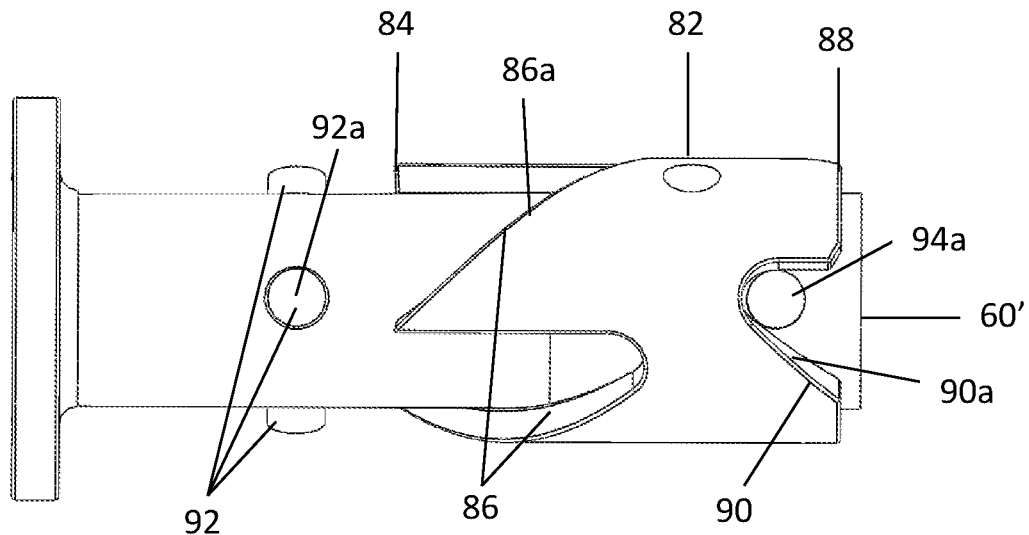
FIG. 19 is a top view of a hub collar and actuation shaft of the rotation mechanism of FIG. 18 with the hub collar in a first position.
Figure 20:
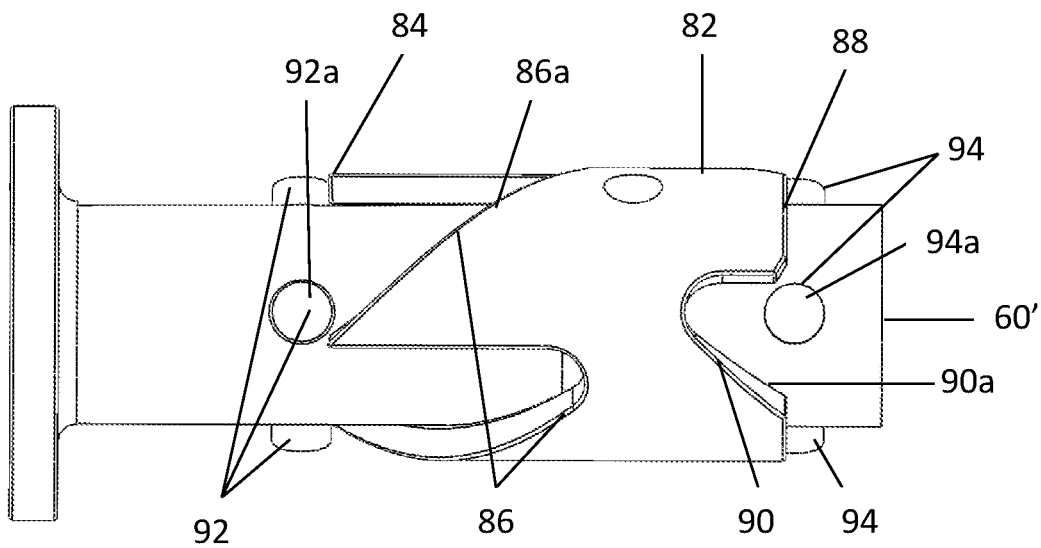
FIG. 20 is a top view of the hub collar and actuation shaft of the rotation mechanism of FIG. 18 with a hub collar in a second position.
Figure 21:
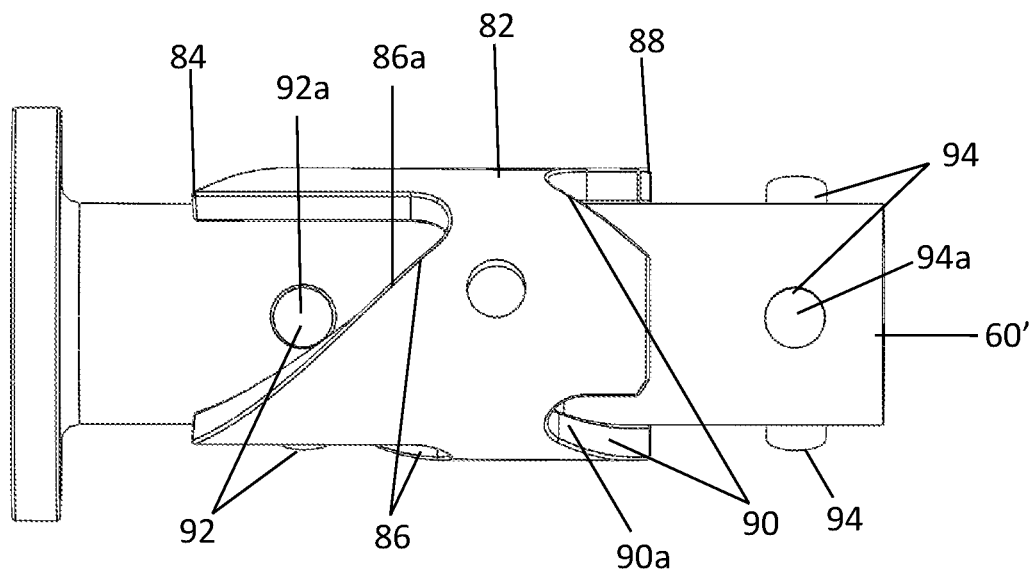
FIG. 21 is a top view of the hub collar and actuation shaft of the rotation mechanism of FIG. 18 with a hub collar in a third position.
Figure 22:
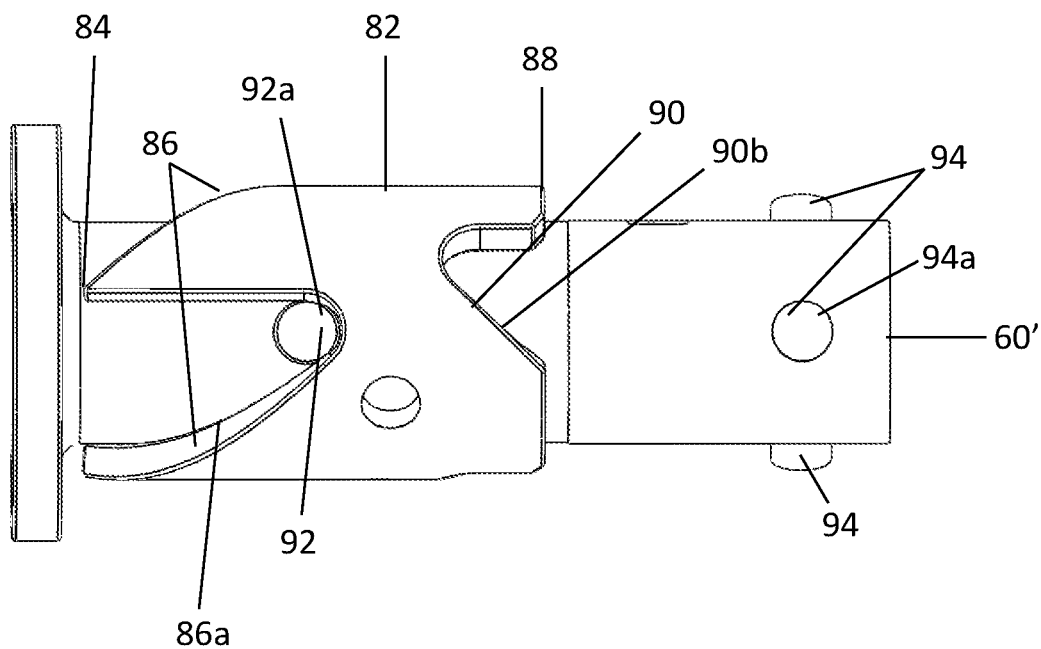
FIG. 22 is a top view of the hub collar and actuation shaft of the rotation mechanism of FIG. 18 with a hub collar in a fourth position.
Figure 23:
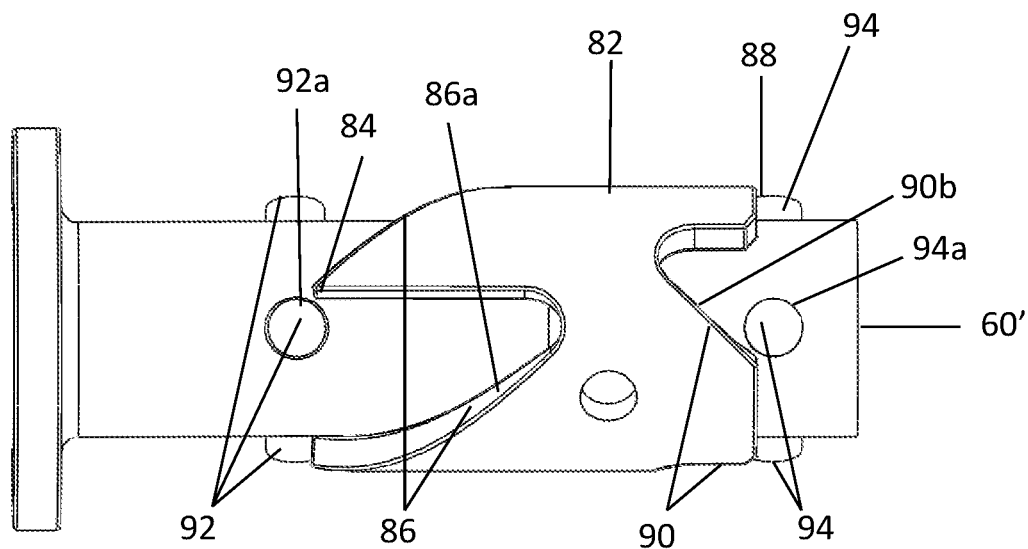
FIG. 23 is a top view of the hub collar and actuation shaft of the rotation mechanism of FIG. 18 with a hub collar in a fifth position.
Figure 24:
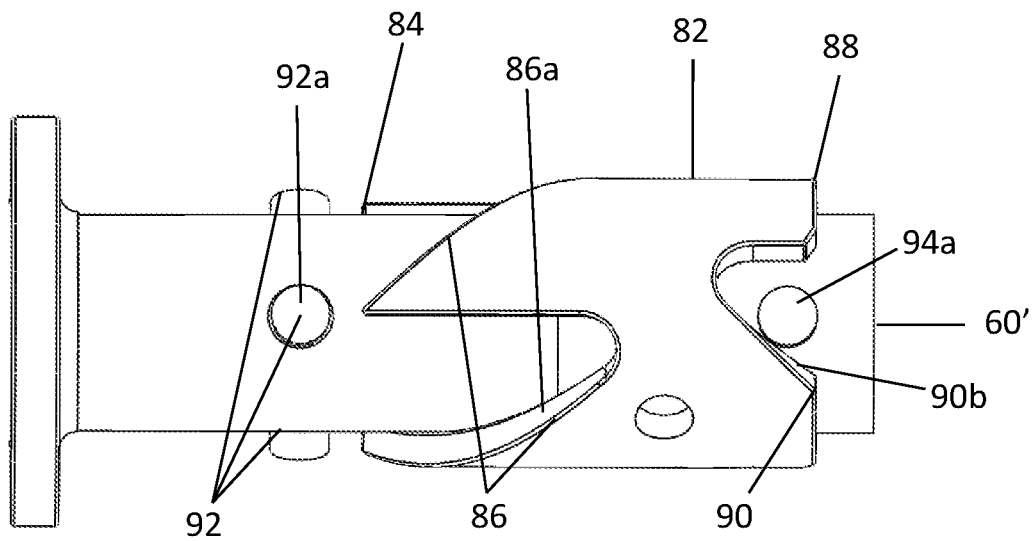
FIG. 24 is a top view of the hub collar and actuation shaft of the rotation mechanism of FIG. 18 with a hub collar in a sixth position.

With reference to FIGS. 19-25, an operation sequence of the rotation mechanism 70' to rotate the actuation shaft 60' from a first orientation to a second orientation is illustrated. FIG. 19 illustrates a schematic view of the hub collar 82 and actuation shaft 50' in a first orientation. In the first orientation, a first projection 94a of the second plurality of projections 94 rests in a first recess 90a of the plurality of recesses 90, and a first projection 92a of the first plurality of projections is positioned adjacent a first ramp 86a of the plurality of ramps 86.

Figure 25:
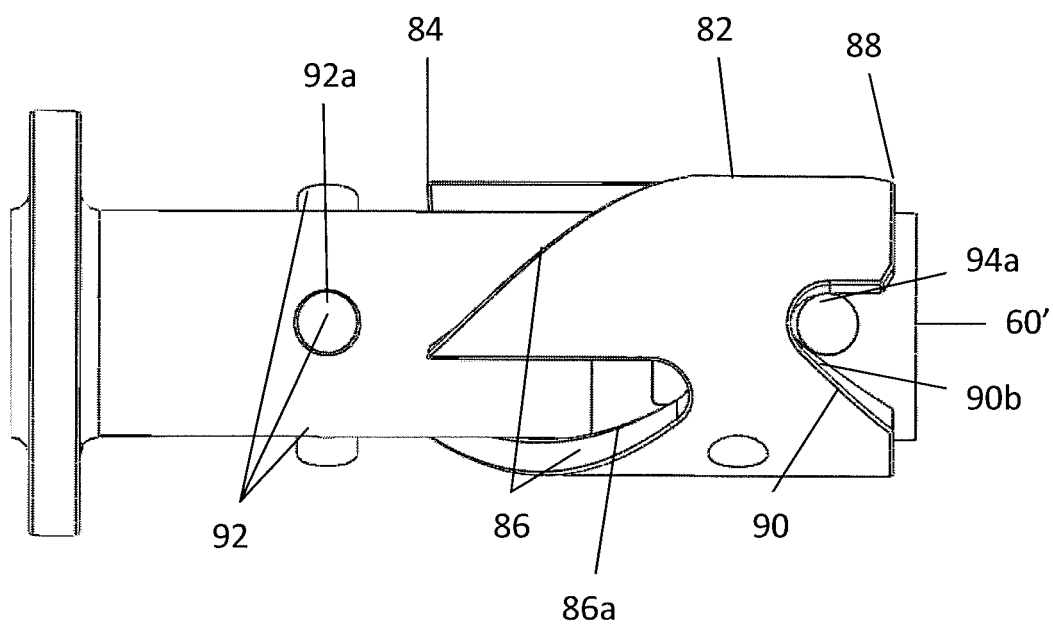
FIG. 25 is a top view of the hub collar and actuation shaft of the rotation mechanism of FIG. 18 with a hub collar in a seventh position.

With reference to FIGS. 19-22, an operation sequence of the rotation mechanism 70' as the slidable switch 80 is advanced distally is illustrated. As the slidable switch 80 is advanced distally with respect to the housing of the handle assembly, the hub collar 82 translates distally, bringing the first plurality of projections 92 into sliding engagement with the plurality of ramps 86 of the hub collar 82 (illustrated in FIG. 20). Further distal advancement of the slidable switch 80 and hub collar 82 relative to the housing of the handle assembly advances the first plurality of projections 92 over the plurality of ramps 86 (illustrated in FIGS. 21 and 22). An angular profile of the ramps 86 acts as a camming surface such that travel of the first plurality of projections 92 along the plurality of ramps 86 rotates the actuation shaft 60'. Once the slidable switch reaches the distal most end of its travel, the spring 98 biases the hub collar 82 and sliding switch 80 proximally with respect to the housing of the handle assembly 40. As the hub collar 82 returns to a proximal position, the second plurality of projections 94 engages the plurality of recesses 90 (illustrated in FIGS. 23-25). As illustrated in FIG. 25, following an actuation cycle of the slidable switch 80, the first projection 94a of the second plurality of projections 94 has been positioned in the second recess 90b of the plurality of recesses such that the actuation shaft 60' has been positioned in a second orientation rotated 120 degrees from the first orientation. Subsequent actuation cycles of the slidable switch 80 rotate the actuation shaft in discrete 120 degree increments.

In other embodiments, the rotation mechanism can comprise a handle directly connected to the actuation shaft. For example, a proximal end of the actuation shaft can be connected to a handle 70" (FIG. 1) extending proximally from the housing. Rotation of the handle relative to the longitudinal axis rotates the actuation shaft to configure the handle assembly in one of an open/close mode, a forward mode, or a reverse mode.

Although this application discloses certain preferred embodiments and examples, it will be understood by those skilled in the art that the present inventions extend beyond the specifically disclosed embodiments to other alternative embodiments and/or uses of the invention and obvious modifications and equivalents thereof. Further, the various features of these inventions can be used alone, or in combination with other features of these inventions other than as expressly described above. Thus, it is intended that the scope of the present inventions herein disclosed should not be limited by the particular disclosed embodiments described above, but should be determined only by a fair reading of claims which follow.

What is claimed is:

1. A handle assembly for a surgical stapler, the handle assembly comprising:
   a housing;
   a movable handle pivotably coupled to the housing and movable from an open position to a closed position; and
   an actuation mechanism comprising:
      a forward driver movable by the movable handle;
      a reverse driver;
      an idler coupling the forward driver to the reverse driver; and
      an actuation shaft having a longitudinal axis, the actuation shaft being longitudinally slidable relative to the housing and selectively rotatable about the longitudinal axis between a first orientation and a second orientation.

2. The handle assembly of claim 1, wherein the forward driver is engageable with the actuation shaft with the actuation shaft in the first orientation.

3. The handle assembly of claim 1, wherein the reverse driver is engageable with the actuation shaft in the second orientation.

4. The handle assembly of claim 3, wherein the reverse driver is disengaged from the actuation shaft in the first orientation.

5. The handle assembly of claim 1, wherein the actuation mechanism further comprises an opening driver engageable with the actuation shaft with the actuation shaft in the second orientation.

6. The handle assembly of claim 5, wherein the idler comprises a slot formed therein and the opening driver comprises a pin disposed in the slot of the idler.

7. The handle assembly of claim 5, wherein the actuation shaft comprises an opening recess formed thereon, the opening recess engageable with the opening driver with the actuation shaft in the second orientation.

8. The handle assembly of claim 1, wherein the idler couples the forward driver to the reverse driver such that movement of the trigger moves the forward driver in a first direction and moves the reverse driver in a second direction opposite the first direction.

9. The handle assembly of claim 8, wherein the forward driver is translatable distally with respect to the longitudinal axis responsive to movement of the movable handle from the open position to the closed position; and wherein the reverse driver is translatable proximally with respect to the longitudinal axis responsive to movement of the movable handle from the open position to the closed position.

10. The handle assembly of claim 1, wherein the actuation shaft comprises an advancing rack, and wherein the forward driver is engaged with the advancing rack when the actuation shaft is in the first orientation.

11. The handle assembly of claim 10, wherein the actuation shaft comprises a reversing rack, and wherein the reverse driver is engaged with the reversing rack when the actuation shaft is in the second orientation.

12. The handle assembly of claim 11, wherein the advancing rack is angularly offset from the reversing rack relative to the longitudinal axis.

13. The handle assembly of claim 12, wherein the advancing rack is angularly offset from the reversing rack by approximately 90 degrees.

14. The handle assembly of claim 1, further comprising a rotation mechanism engaged with the actuation mechanism to selectively rotate the actuation shaft between the first orientation and the second orientation.

15. A handle assembly for a surgical stapler, the handle assembly comprising:
   a stationary handle;
   a movable handle coupled to the stationary handle and movable from an open position spaced apart from the stationary handle to a closed position adjacent the stationary handle;
   an actuation shaft having a longitudinal axis, the actuation shaft longitudinally slidable along the longitudinal axis relative to the stationary handle and selectively rotatable about the longitudinal axis between a firing mode and a reverse mode; and a rotation mechanism configured to orient the actuation shaft in one of the firing mode and the reverse mode, the rotation mechanism comprising a slider extending transversely to the longitudinal axis, the slider coupled to the actuation shaft such that movement of the slider transverse to the longitudinal axis rotates the actuation shaft.

16. The handle assembly of claim 15, wherein the slider comprises a rack formed thereon and the rotation mechanism further comprises a gear in meshed engagement with the rack, the gear rotatably fixed to the actuation shaft and longitudinally slidable along the actuation shaft.

17. The handle assembly of 16, wherein the slider is positionable in a first position extending from a first side of the housing in which the actuation shaft is in the firing mode and a second position extending from a second side of the housing opposite the first side in which the actuation shaft is in the reverse mode.

18. The handle assembly of claim 15, wherein the actuation shaft comprises a first rack engageable with the movable handle with the actuation shaft in the firing mode.

19. The handle assembly of claim 18, wherein the actuation shaft further comprises a second rack engageable with the moveable handle with the actuation shaft in the reverse mode.

20. The handle assembly of claim 19, wherein the first rack is disengaged from the movable handle with the actuation shaft in the reverse mode.

\* \* \* \* \*